(12) United States Patent
Aditya et al.

(10) Patent No.: US 10,058,577 B2
(45) Date of Patent: Aug. 28, 2018

(54) THERMO-STABLE STRAINS, PRODUCTS AND METHODS THEREOF

(71) Applicant: TRIPHASE PHARMACEUTICALS PVT. LTD., Karnataka, Mysore (IN)

(72) Inventors: Desiraju Aditya, Mysore (IN); Desiraju Shrilakshmi, Mysore (IN); Sharieff Irfanulla, Mysore (IN); Prakash Abhilash, Mysore (IN)

(73) Assignee: TRIPHASE PHARMACEUTICALS PVT. LTD., Mysore (IN)

( * ) Notice: Subject to any disclaimer, the term of this patent is extended or adjusted under 35 U.S.C. 154(b) by 5 days.

(21) Appl. No.: 15/115,446

(22) PCT Filed: Sep. 30, 2015

(86) PCT No.: PCT/IB2015/057497
§ 371 (c)(1),
(2) Date: Jul. 29, 2016

(87) PCT Pub. No.: WO2016/051358
PCT Pub. Date: Apr. 7, 2016

(65) Prior Publication Data
US 2017/0157184 A1 Jun. 8, 2017

(30) Foreign Application Priority Data

Oct. 1, 2014 (IN) .......................... 4978/CHE/2014

(51) Int. Cl.
| | |
|---|---|
| *A61K 35/747* | (2015.01) |
| *C12R 1/23* | (2006.01) |
| *C12R 1/25* | (2006.01) |
| *A23L 33/135* | (2016.01) |
| *A23L 23/00* | (2016.01) |
| *A23G 1/42* | (2006.01) |
| *A21D 8/04* | (2006.01) |
| *A23G 3/36* | (2006.01) |
| *A23F 3/16* | (2006.01) |

(52) U.S. Cl.
CPC .............. *A61K 35/747* (2013.01); *A21D 8/04* (2013.01); *A23G 1/423* (2013.01); *A23L 23/00* (2016.08); *A23L 33/135* (2016.08); *C12R 1/23* (2013.01); *C12R 1/25* (2013.01); *A23F 3/16* (2013.01); *A23G 3/366* (2013.01); *A23V 2002/00* (2013.01); *A23Y 2220/03* (2013.01); *A23Y 2220/67* (2013.01)

(58) Field of Classification Search
CPC ........... A21D 8/04; A23G 1/423; A23L 23/00; A23V 2002/00; A23Y 2220/03; C12R 1/23; A23F 3/16
See application file for complete search history.

(56) References Cited

U.S. PATENT DOCUMENTS

| | | | |
|---|---|---|---|
| 3,689,640 A | 9/1972 | Shahani et al. | |
| 6,562,336 B2* | 5/2003 | De Simone | A61K 35/744 424/93.3 |
| 7,052,898 B2 | 5/2006 | Hansen et al. | |
| 8,137,952 B2* | 3/2012 | Hakansson | A21D 8/045 426/61 |
| 2004/0077008 A1 | 4/2004 | Peters | |
| 2013/0029384 A1 | 1/2013 | Cerdobbel et al. | |

OTHER PUBLICATIONS

Feb. 5, 2016 International Search Report issued in International Patent Application No. PCT/IB2015/057497.
Feb. 5, 2016 Written Opinion issued in International Patent Application No. PCT/IB2015/057497.

* cited by examiner

*Primary Examiner* — Lynn Y Fan
(74) *Attorney, Agent, or Firm* — Oliff PLC

(57) ABSTRACT

The present disclosure relates to thermo-stable/heat stable strain(s) of micro-organisms, obtaining such thermo-stable strains and incorporating them into food products. These strains are able to survive high temperatures for longer periods of time and thus food products containing such strains are therapeutically effective and beneficial for general health.

12 Claims, 12 Drawing Sheets

Specification includes a Sequence Listing.

THERMO-STABLE STRAINS, PRODUCTS AND METHODS THEREOF

TECHNICAL FIELD

The present disclosure relates to the field of microbiology and industrial biotechnology. In particular, the present disclosure relates to thermo-stable or heat stable strain(s) of micro-organisms, probiotic food products comprising thermo-stable strain(s), method of preparing food products comprising thermo-stable strain(s) and method of managing various disorders using the thermostable strains.

BACKGROUND AND PRIOR ART OF THE DISCLOSURE

The genus *Lactobacillus* is a varied group of lactic acid bacteria which has important implications in food fermentation and is commonly found in fermented food products like yogurt. The ability of these bacteria to colonize a variety of habitats is a direct consequence of the wide metabolic versatility of this genus of bacteria i.e. *Lactobacillus*.

It is known that the presence of *Lactobacillus* species in the gut has following advantages:
  Ample production of lactic acid in the gut lowers the pH of the gut to prevent bacteria such as *Clostridium, Salmonella, Shigella*, etc.
  Decreases production of a variety of toxic or carcinogenic metabolites.
  Helps in absorption of minerals, especially Calcium, due to increased intestinal acidity.
  Helps in production of β-D-galactosidase enzymes that break down lactose.
  Produce a wide range of antimicrobial substances such as—Acidophilin, Bacteriocin, etc. to control pathogenic bacteria.
  Production of Vitamins (especially Vitamin B and vitamin K).

Thus, Lactobacilli find application in food and feed biotechnology, including their use as probiotics, dairy starters, silage inoculants, and microbial cell factories. They are incorporated in nutraceuticals food items to treat disorders relating to the gut like colic infections, inflammation of colon, urinary and genital infections. Therefore, there is a huge demand for Lactobacilli food supplements in the market. Moreover, such food items can be a boon to people who suffer from lactose intolerance, by avoiding intake of milk and milk products. Food items/products containing Lactobacilli have been produced, in the form of probiotic drinks, probiotic curd etc. Probiotics incorporated in foods have various advantages when compared to consuming the probiotics separately:
  Synergistic effect between components of foods and probiotic cultures.
  The natural buffering of stomach acid by food also enhances the stability of consumed probiotics.
  Dairy products containing probiotics provide a number of high quality nutrients including Calcium, protein, bioactive peptides, sphingo lipids, and conjugated linoleic acids.
  Incorporating foods containing probiotics into daily food choices can become a lifestyle habit.

The biggest drawback associated with manufacturing food products containing Lactobacilli is the issue of heat/thermal sensitivity of Lactobacilli, i.e. these bacteria lose their viability at high temperatures. During the process of manufacturing of various food items, as the temperature rises, the Lactobacilli are not able to survive and die in the process. Since it is well known that probiotics have to be alive when administered, one of the main concerns resides in the 'viability' and 'reproducibility' of Lactobacilli on a large scale of the observed results, as well as the viability and stability of Lactobacilli during use and storage and finally the ability to survive in the intestinal ecosystem.

Therefore, only products containing live organisms shown in reproducible human studies to confer a health benefit can actually claim to be a probiotic. The correct definition of health benefit, backed with scientific evidence, is a strong element for the proper identification and assessment of the effect of a probiotic. This aspect represents a major challenge for scientific and industrial investigations because several difficulties arise, such as variability in the site for probiotic use (oral, vaginal, intestinal) and mode of application.

Another drawback associated with such probiotic food products is that they need to be transported and stored effectively so as to maintain the viability of these probiotics which have been incorporated in the food products. A common method for storing probiotic food products is cold storage, which is an expensive and complicated process. Cold chains are common in the food and pharmaceutical industries and also in some chemical shipments. One common temperature range for a cold chain in pharmaceutical industries is 2° C. to 8° C., but the specific temperature (and time at temperature) tolerances depend on the actual product being shipped. Unique to fresh produce cargos, the cold chain requires to additionally maintain product specific environment parameters which include air quality levels (carbon dioxide, oxygen, humidity and others), which makes this the most complicated cold chain to operate.

To overcome the drawbacks of prior art, the present disclosure provides thermo-stable strain(s) and food or food products comprising the thermo-stable strain(s) which addresses and manages gut and immune associated problems, simultaneously eliminating the need for cold storage, which is an enormous cost saving for the supply chain.

STATEMENT OF THE DISCLOSURE

Accordingly, the present disclosure relates to a food product comprising a thermostable *Lactobacillus* microorganism, wherein the thermostable microorganism is selected from group comprising *Lactobacillus plantarum* with ATCC SD No. 6863 and *Lactobacillus acidophilus* with ATCC SD No. 6864; a method of preparing a food product, said method comprising act of combining a thermostable strain selected from group *Lactobacillus plantarum* with ATCC SD No. 6863 and *Lactobacillus acidophilus* with ATCC SD No. 6864, with component of the food product during or after preparation of the food product; a thermostable *Lactobacillus* microorganism selected from group comprising *Lactobacillus plantarum* with ATCC SD No. 6863 and *Lactobacillus acidophilus* with ATCC SD No. 6864; a thermostable microorganism for use in managing a disorder in a subject, wherein the microorganism is selected from group comprising *Lactobacillus plantarum* with ATCC SD No. 6863 and *Lactobacillus acidophilus* with ATCC SD No. 6864; and a method of managing a disorder in a subject, wherein the method comprises step of administering to the subject, microorganism selected from group comprising *Lactobacillus plantarum* with ATCC SD No. 6863 and *Lactobacillus acidophilus* with ATCC SD No. 6864.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

DETAILED DESCRIPTION OF THE DISCLOSURE

Figure 1:
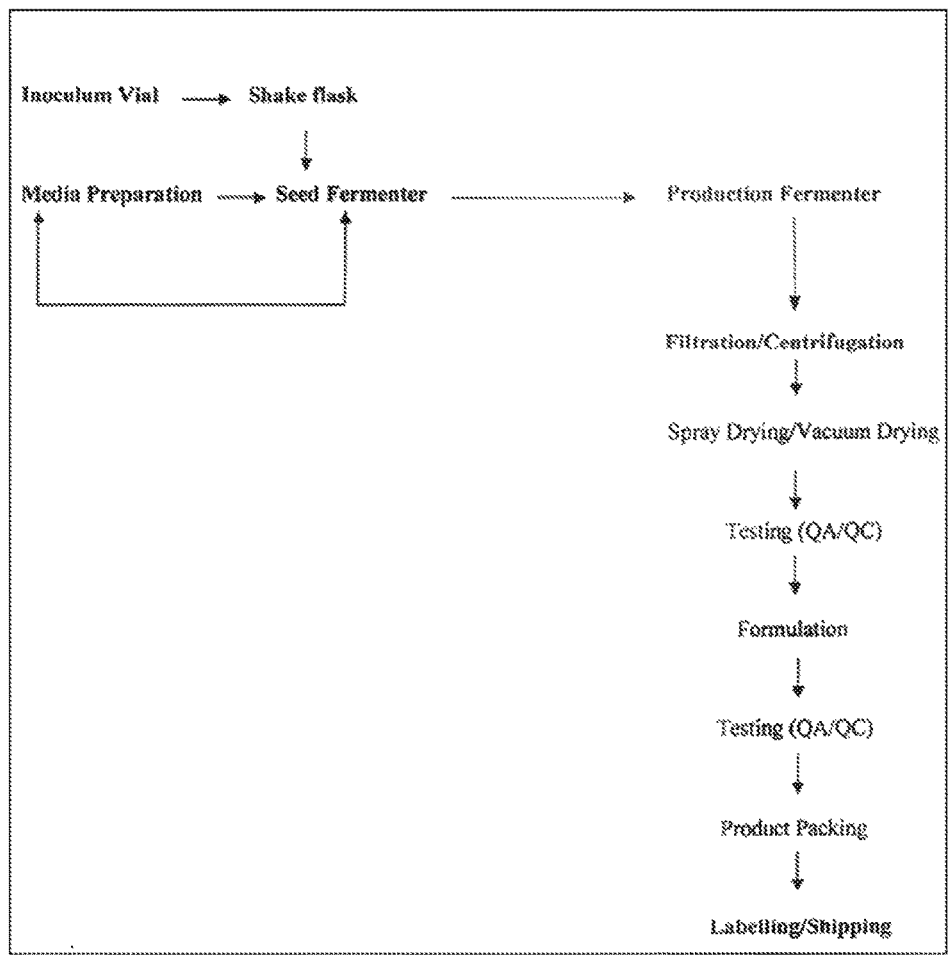
FIG. 1 depicts the flow chart for the manufacture of Probiotic food of the present disclosure.

The present disclosure relates to a food product comprising a thermostable Lactobacillus microorganism, wherein the thermostable microorganism is selected from group comprising Lactobacillus plantarum with ATCC SD No. 6863 and Lactobacillus acidophilus with ATCC SD No. 6864.

The present disclosure also relates to a method of preparing a food product, said method comprising act of combining a thermostable strain selected from group Lactobacillus plantarum with ATCC SD No. 6863 and Lactobacillus acidophilus with ATCC SD No. 6864; with component of the food product during or after preparation of the food product.

In an embodiment of the present disclosure, the food product is selected from group comprising beverage, yogurt, dairy product, nectar, fruit juice, energy drink, bakery food, chocolate, cereal and soup.

In another embodiment of the present disclosure, the thermostable microorganism is viable at temperature ranging from about 25° C. to 250° C.

The present disclosure also relates to a thermostable Lactobacillus microorganism selected from group comprising Lactobacillus plantarum with ATCC SD No. 6863 and Lactobacillus acidophilus with ATCC SD No. 6864.

In an embodiment of the present disclosure, the Lactobacillus plantarum has genomic sequence set forth in SEQ ID No.1.

In another embodiment of the present disclosure, the Lactobacillus acidophilus has genomic sequence set forth in SEQ ID No.2.

In yet another embodiment of the present disclosure, the thermostable microorganism is viable at temperature ranging from about 25° C. to 250° C.

The present disclosure also relates to a thermostable microorganism for use in managing a disorder in a subject, wherein the microorganism is selected from group comprising Lactobacillus plantarum with ATCC SD No. 6863 and Lactobacillus acidophilus with ATCC SD No. 6864.

The present disclosure also relates to a method of managing a disorder in a subject, wherein the method comprises step of administering to the subject, microorganism selected from group comprising Lactobacillus plantarum with ATCC SD No. 6863 and Lactobacillus acidophilus with ATCC SD No. 6864.

In an embodiment of the present disclosure, the disorder is selected from group comprising diarrhea, antibiotic-associated diarrhea, irritable bowel syndrome, constipation, lactose intolerance, vaginal infection, intestinal infection, inflammatory bowel disease, and combinations thereof.

In another embodiment of the present disclosure, the microorganism is in free form or form of food product.

In yet another embodiment of the present disclosure, the subject is selected from group comprising animal and human being.

The present disclosure relates to thermo-stable strain(s) of micro-organism(s).

In an embodiment of the present disclosure, the microorganism(s) is from Lactobacillus species.

In an embodiment of the present disclosure, the thermostable strain(s) of the present disclosure have a tolerance to high temperatures.

In the present disclosure, the term "thermostable" is intended to convey that the strains are able to survive at high temperatures for a long period of time.

In embodiments of the present disclosure, the strains are viable, tolerant and resistant to high temperatures.

In embodiments of the present disclosure, the thermostable strains are isolated thermostable strains.

In embodiments of the present disclosure, the thermostable strains depict viability ranging from 1% to 99%.

In embodiments of the present disclosure, the viability of the strains is dependent on environmental factors such as pH, temperature and time period.

In embodiments of the present disclosure, viability of the thermostable strains is equal to and greater than $1.0$-$1.5 \times 10^9$ colony forming units (cfu) is considered to be satisfactory for use in a food product.

It is to be noted that the number of cfu's in a product differs depending on the mode of products. For example, for tablets/sachets/capsules, it is expressed per tablet/sachet/capsule, whereas, in food example like chocolate/muffin/cookie/bread it is expressed based on the serving.

Probiotic dosing varies depending on the product and specific indication. No consensus exists about the minimum number of microorganisms that must be ingested to obtain a beneficial effect. Typically, a probiotic should contain several billion microorganisms to increase the likelihood of adequate gut colonization. For Lactobacilli, typical doses used range from 1-20 billion colony-forming units per day.

In embodiments of the present disclosure, the thermostable strain is mixed or combined with a food component during the preparation of the food product.

In embodiments of the present disclosure, the thermostable strain is mixed or combined with the food product after preparation of the food product.

In an embodiment of the present disclosure, 1.00 g of a spray dried powdered sample of *Lactobacillus acidophilus* TSP-La1 contains a total viable cell count of 82.0 billion cfu/gm.

In an embodiment of the present disclosure, 1.00 g of a spray dried powdered sample of *Lactobacillus plantarum* TSP-Lp1 contains a total viable cell count of 248.25 billion cfu/gm.

In embodiments, the temperature ranges from about 25° C. to about 250° C.

In embodiments of the present disclosure, the free form of the strains of the disclosure is selected from group comprising spray dried capsule, powder, tablet, sachet, ez melt, and chewable tablet.

In the form of a food product, the spray dried powder is used in making different foods example Gummies, chocolate, cookies, muffins, bread, etc.

In particular embodiments of the present disclosure, the strains have the ability to perform their functions in different food products even at higher temperatures, which makes them therapeutically effective.

*Lactobacillus acidophilus* is a naturally occurring beneficial bacterium which supports the health of the intestinal tract. It maintains a healthy microflora by protecting the body against an overgrowth of harmful bacteria, helps improve digestion, protects against gastrointestinal upsets, abdominal pains, constipation and antibiotic-induced diarrhea.

*Lactobacillus plantarum* can live in the stomach for a considerable period. It continuously fights disease and prevents entry of pathogenic microorganisms. It also improves digestive health, helps treat Irritable Bowel Syndrome (IBS), and prevents food allergies.

In the present disclosure, the term "CFU" relates to colony forming units.

In the present disclosure, the term "MIC" relates to Minimum Inhibitory Concentration.

In the present disclosure, the term "TVCC" relates to Total Viable Cell Count.

In the present disclosure, the term "GYEA" relates to "Glucose Yeast Extract Agar".

In the present disclosure, the term "PBS" relates to "Phosphate Buffered Saline."

In the present disclosure, the term beverage includes—Soup, Tea, Coffee, Energy drinks, and fruit juices.

In the present disclosure, the term bakery food includes Bread, Muffins, and Cookies.

The temperature-stable probiotic strains, of *Lactobacillus plantarum* (TSP-Lp1) & *Lactobacillus acidophilus* (TSP-La1) have the ability to withstand harsh manufacturing processes, especially required during making Food/Beverage and in the Pharma industries. Most of the probiotics currently available in the market cannot survive a harsh environment observed during manufacturing and acidic environment of the stomach. These currently available probiotics are enteric coated to withstand harsh conditions. Probiotics that fail to reach intestinal tract alive are not likely to provide digestive and immune support. In the table provided below, the strains of the present disclosure are compared with commercial strains and their advantageous features are highlighted.

TABLE 1

| Strain Name | Parameters | Triphase Strains | Commercial strains |
| --- | --- | --- | --- |
| *Lactobacillus acidophillus* (TSP-La1) | High Temperature stability | Yes | No |
| ATCC-SD 6864 | Non-GMO | Yes | Yes |
| | Enteric Coating | Not required | Required |
| | Refrigeration/ Cold storage | Not required | Required |
| *Lactobacillus plantarum* (TSP-Lp1) | High Temperature stability | Yes | No |
| ATCC-SD 6863 | Non-GMO | Yes | Yes |
| | Enteric Coating | Not required | Required |
| | Refrigeration/ Cold storage | Not required | Required |

In the present disclosure, the term "managing" or "management" or "manage" includes therapeutic and prophylactic activities. It includes treatment and healing of a disease or disorder, or ill effects or side effects of the disease or the disorder. The term also includes prevention of further progress of the disease or disorder, and prevention of further progress of ill effects or side effects of the disease or the disorder. It further includes maintenance of the optimum state in an individual.

In the present disclosure, it is within the knowledge of the person skilled in the art to determine a suitable dosage of the strains and dosage form for administering to a particular subject.

In another embodiment of the present disclosure, the thermo-stable *Lactobacillus* strain is selected from a group comprising *Lactobacillus plantarum* and *Lactobacillus acidophilus*

In yet another embodiment of the present disclosure, the thermo-stable *Lactobacillus* strain is *Lactobacillus plantarum* TSP-Lp1.

The parent strains for the present disclosure have been procured form Microbial Type Culture Collection (MTCC).

In yet another embodiment of the present disclosure, the thermo-stable *Lactobacillus plantarum* is *Lactobacillus plantarum* TSP-Lp1.

The *Lactobacillus plantarum* strain of the present disclosure is also referred to as LP throughout the present disclosure.

In still another embodiment of the present disclosure, the thermo-stable *Lactobacillus acidophilus* is *Lactobacillus acidophilus* TSP-La1.

The *Lactobacillus acidophilus* strain of the present disclosure is also referred to as La throughout the present disclosure.

The novel strains of the present disclosure have been deposited in American Type Culture Collection (ATCC), 10801 University Boulevard, Manassas, Va., 20110 USA on Feb. 17, 2015. The strains have been allotted accession numbers as follows:

*Lactobacillus plantarum* SD 6863 (SD-Safe Deposit)
*Lactobacillus acidophilus* SD 6864 (SD-Safe Deposit)

In yet another embodiment, the thermo-stable strain(s) of the present disclosure are able to withstand temperature ranging from room temperature i.e. about 25° C. to about 250° C.

The present disclosure relates to food product comprising thermo-stable strain(s) of micro-organism(s).

The present disclosure relates to probiotic food products comprising thermo-stable strain(s) of micro-organism(s).

In an embodiment of the present disclosure, micro-organism(s) is from *Lactobacillus* species. In an embodiment of the present disclosure, the food or food product contains micro-organism(s) from *Lactobacillus* species.

In another embodiment of the present disclosure, the *Lactobacillus* strain(s) in food product/probiotic food products is selected from a group comprising *Lactobacillus plantarum* and *Lactobacillus acidophilus* and combinations thereof.

Food products according to the present disclosure may comprise one or more strains selected from the above defined strains. Other mixtures or single thermostable strains are used advantageously within the scope of the present disclosure.

These novel strains survive long periods of storage in room temperature and are endurable. Thus, food products containing the strains of the present disclosure have a long shelf life and are easily included in different food products.

In yet another embodiment, the probiotic food products of the present disclosure comprising thermo-stable strain(s) of *Lactobacillus* provide for enhanced nutrition and help in eliminating disorders relating to gut, the disorder being selected from a group comprising but not limiting to irritable bowel syndrome, different forms of diarrhea, irritable bowel disorder, constipation, lactose intolerance and any combinations thereof and vaginal infections.

In still another embodiment, the food product is selected from a group comprising but not limiting to, beverage, yogurt, dairy product, nectar, fruit juice, energy drink, bakery food, chocolate, cereal, soup and combinations thereof.

In still another embodiment, the food product having heat stable or thermostable strain(s) of micro-organism(s) is referred to as probiotic food products within the ambit of the present disclosure.

In still another embodiment, the present disclosure provides probiotic food products which involve heating at high temperatures, especially those required to make hot beverages like soup, tea, coffee, chocolates, cereals and other food products as the probiotic strains of the present disclosure are able to withstand high temperatures.

In still another embodiment, the thermo-stable strain(s) in the food product of the present disclosure is able to withstand high temperature ranging from room temperature of about 25° C. to about 250° C.

In yet another embodiment, the probiotic food products of the present disclosure eliminate the requirement of cold storage and thus are economically beneficial to the end user.

In yet another embodiment, the food products of the present disclosure having heat stable strain(s) of the present disclosure when heated at a high temperature are not affected in terms of taste or efficacy of the probiotic culture.

The present disclosure relates to a process of obtaining heat stable strain(s) of micro-organism(s) comprising act of fermentation and spray drying.

The present disclosure also relates to a process of manufacturing a food product comprising thermo-stable strain(s) of micro-organism(s), wherein the process comprises act of mixing the thermo-stable strain(s) with at least one of the components of the food product at any time during preparation of the food product In an embodiment of the present disclosure, the probiotic food of the present disclosure has various advantages which are listed below:

Able to survive the passage through the digestive system.
Able to attach to the intestinal epithelia and colonise effectively and multiply. Able to maintain good viability.
Able to utilise the nutrients and substrates in a normal diet.
Non-pathogenic and non-toxic.
Capable of exerting a beneficial effect on the host. Stability of desired characteristics during processing, storage and transportation.
Anti-inflammatory, anti-mutagenic and immuno-stimulatory in nature.

Thus, the present disclosure provides heat stable/thermo-stable microbial strain(s) capable of surviving high temperatures, wherein these strain(s) incorporated in foods serve as probiotic foods and manage diseases/disorders.

Throughout the specification, the food product comprising thermo-stable microbial strain(s) of the disclosure is also alternatively referred to as "Probiotic food" or "Probiotic food product" and the terms have the same meaning and scope.

Throughout the specification, the thermo-stable microbial strain(s) of the disclosure are alternatively referred to as "heat stable microbial strain(s)", "heat stable/thermo-stable microbial strain(s)".

The present disclosure is further elaborated with reference to the following examples, which are only illustrative in nature and should not be construed to limit the scope of the present disclosure in any manner.

EXAMPLES

Example 1: Method for Producing Probiotics i.e. Heat Stable Strains of *Lactobacillus plantarum*

The various steps involved in the production of probiotics are provided below briefly:

Fermentation/Perfusion Technology:

The mother strain of *Lactobacillus* spp. is grown in media at optimized temperatures. The thermo-stable *Lactobacillus* species of the present disclosure are manufactured using a fermentation procedure by employing perfusion mode. The perfusion technology improves the cell densities during fermentation.

Spray Drying:

This step is carried out in order to obtain powdered form of probiotics, wherein the medium containing the strains is sprinkled on to the walls of the dryer and dried by subjecting them to a temperature of about 90° C.-120° C. The down streaming process for the *Lactobacillus* species is completed with a custom built spray drier wherein the microbial strains/probiotics are powdered.

Testing (QA/QC):

A complete microbiological analysis is performed for viable count colony forming units/g. of *Lactobacillus* spp on the spray dried product.

Example 2: Method of Formulating Food Products Containing *Lactobacillus* Heat Stable Strains The flow chart for the manufacture of probiotic food of the present disclosure is provided in FIG. 1 of the present disclosure.

As observed, the probiotic culture is taken in an inoculum vial and then added to a shake flask. The medium prepared is added into the Seed fermenter along with the probiotic strain from the shake flask. The entire culture is then transferred into a Production fermenter and allowed to grow. The cells of the culture are then filtered or centrifuged, and spray dried or vacuum dried to obtain the cells in powder form. This is followed by Formulation of the probiotic, after which the product is packed and labeled.

After preparation of the probiotic strains, they are formulated into the food items in order to produce various food products such as but not limiting to beverages, yogurt, dairy products, nectars, fruit juices, energy drinks, bakery food, chocolates, cereals, soup and combinations thereof.

Probiotic Gummies Preparation:
Ingredients for Batch Size of 230 gm:
Phase A—Water—36 gm and Gelatin—21.0 gm
Phase B—Corn syrup—66.4 gm, Water—66.3 gm and Sugar—90.2 gm
Phase C—Citric acid—0.9 gm, Colour Red #40—1.2 gm and Mixed berry flavour—0.9 gm
*Lactobacillus acidophilus*—3.0 gm (From $1.5 \times 10^9$)
*Lactobacillus plantarum*—0.28 gm (From $1.9 \times 10^{11}$)
Temperature: 70° C.
Method of Preparation:
1. The ingredient of Phase A is weighed and is mixed and is kept at room temperature for 10-15 minutes.
2. The ingredients of the Phase B are weighed and dissolved. The phase B ingredients are kept for boiling until the mixture formed is thick and viscous.
3. Then ingredients of the Phase C is weighed & dissolved.
4. Then ingredients of Phase A and B are mixed uniformly and is added to ingredients of
Phase C and mixed for 2-3 minutes.
5. When the temperature is around 70° C., the probiotics (*Lactobacillus acidophilus/Lactobacillus plantarum*) is weighed as per requirement (500 million cfu/gummy) is added and is mixed uniformly.
6. It is then poured into the moulds and kept for refrigeration for 45 minutes, for the gummies to set.
7. After 45 minutes the gummies are subjected to conditioning for 24 hours. The gummy samples are taken up for total viable count analysis to check viability of probiotic.

Probiotic Soup Preparation:
Ingredients for Batch Size of 100 ml:
Knorr Soup (Ready-made)—7.5 gm
*Lactobacillus acidophilus*—0.75 gm (From $1.6 \times 10^9$)
*Lactobacillus plantarum*—0.065 gm (From $2.48 \times 10^{11}$)
Temperature: 55° C.
Method of Preparation:
1. A known amount (7.5 gm) of the Knorr soup is mixed with water (100 ml) so that there is no formation of lumps.
2. It is placed on a stove and brought to boil while stirring continuously, then simmered for 3 minutes.
3. After 3 minutes the soup temperature is brought down to 55.0 and maintained.
4. When the soup temperature is at 55° C., the probiotic (*Lactobacillus acidophilus/Lactobacillus plantarum*) is weighed as per requirement (160 million cfu/serving), added and mixed thoroughly.
5. The soup temperature is maintained at 55.0 and samples of the soup are drawn at 5th, $10^{th}$ & 15th minute respectively.
6. Then the samples of different time intervals are taken up for Total viable count analysis to check the percentage of viable probiotic.

Probiotic Chocolate Preparation:
Ingredients Batch Size of 25 g:
Wilton Candy Melts (Readymade chocolates chips)—25 gm
*Lactobacillus acidophilus*—1.5 gm (From $1.6 \times 10^9$)
*Lactobacillus plantarum*—0.13 gm (From $1.9 \times 10^{11}$)
Temperature: 70° C.
Method of Preparation:
1. The pre-weighed chocolates chips are subjected to heating in the oven at 70.0 for 1 to 2 minutes until the chocolate chips melt.
2. Once the chocolate chips are melted and temperature is around 70° C., the probiotic (*Lactobacillus acidophilus/Lactobacillus plantarum*) is weighed as per requirement (100 million cfu/chocolate) is added and mixed thoroughly for 2 minutes to get a uniform distribution.
3. Then it is refrigerated for 20 minutes for the chocolate to set and then taken up for Total viable count analysis to check the percentage of viable probiotic.

Probiotic Bread Preparation:
Ingredients for Batch Size of 20 gm:
All-purpose flour—10.0 gm
Baking soda—0.4 gm
Salt—0.1 gm
Butter—1.23 gm
Milk—8.08 gm
*Lactobacillus acidophilus*—0.7 gm (From $1.44 \times 10^{11}$)
*Lactobacillus plantarum*—0.52 gm (From $2.38 \times 10^{11}$)
Temperature: 240° C.
Baking Time: 10 minutes
Method of Preparation:
1. The bread dough is prepared using all-purpose flour, baking soda, salt, butter, milk and probiotic strain (*Lactobacillus acidophilus/Lactobacillus plantarum*) is added to it.
2. Initially the dough is prepared by adding part amount of all-purpose flour, milk and part amount of probiotic (*L. acidophilus/L. plantarum*) and mixed thoroughly for 10 to 15 minutes.
3. The dough is kept at room temperature for 42 hours and the remaining probiotic strain (*L. acidophilus/L. plantarum*) is kept for rehydration for 42 hours at room temperature.
4. After 42 hours the remaining ingredients like (Butter, milk) are mixed with the dough and kneaded for 15-20 minutes till it is not moist and sticky.
5. Then the dough is greased & kept for proofing for 2 hours at room temperature.
6. Then the dough is baked at 240.0 for 10 minutes.
7. After this, the bread is cooled for 10-15 minutes.
8. Then the bread is taken up for total viable cell count analysis to check the viability of probiotic.

Probiotic Muffin Preparation:
Ingredients for Batch Size of 20 gm:
All-purpose flour—4.82 gm
Baking powder—0.329 gm
Sugar—2.85 gm
Unsalted butter—4.82 gm
Egg—4.3 gm
Dark chocolate chips—2.85 gm
*Lactobacillus acidophilus*—1.42 gm (From $1.4 \times 10^{11}$)
*Lactobacillus plantarum*—0.572 gm (From $1.9 \times 10^{11}$)
Temperature: 160° C.
Baking Time: 15 minutes
Method of Preparation:
1. The probiotics (*Lactobacillus acidophilus/Lactobacillus plantarum*) powder is suspended in 0.9% NaCl overnight (15-17 hours).
2. The muffin batter is prepared using unsalted butter, sugar and egg is beaten together for uniform mixing, to this the overnight probiotic (*Lactobacillus acidophilus/Lactobacillus plantarum*) powder is added to it.
3. The dry ingredients (All-purpose flour, baking powder, sugar are then weighed and are added to the liquid batter and mixed thoroughly for 5-10 minutes.
4. The muffin mould is then greased and the batter is kept for proofing for 1 hour at room temperature.
5. The oven is kept for pre-heating and the muffin batter is baked at 160.0 for 15 minutes.
6. After baking, the muffin is cooled for 5-10 minutes at room temperature.
7. Then the muffin is taken up for total viable count analysis to check the viability of probiotic.

Probiotic Tea Powder:
Ingredients:
Twining's Tea & Brooke Bond—2.0 gm
*Lactobacillus acidophilus*—0.1682 gm (From $1.44 \times 10^{11}$)
*Lactobacillus plantarum*—0.001 gm (From $1.9 \times 10^{11}$)
Temperature: 50° C., 60° C. & 70° C.
Method of Preparation:
1. The pre-weighed tea bag is taken and is brewed at 100.0 for 2 minutes.
2. The temperature of tea solution is then brought down to 50° C., 60° C. and 70° C. and maintained.
3. Then the probiotic (*Lactobacillus acidophilus/Lactobacillus plantarum*) is weighed as per requirement (100 million cfu/tea bag) is introduced in the tea solution and mixed.
1. The tea solution temperature is maintained at 50° C., 60° C. and 70° C., samples of the tea solution are drawn at 1st minutes, 3rd minutes, 5th minutes, 7th minute and 10th minute respectively.
2. Then the samples of different time intervals are taken up for Total viable count analysis to check the percentage of viable probiotic.

Probiotic Cookie:
Ingredients for Batch Size of 15 gm:
All-purpose flour—7.51 gm
Baking powder—0.237 gm
Sugar—2.37 gm
Unsalted butter—2.68 gm
Milk—1.426 gm
Salt—0.01 gm
Vanilla essence—0.118 gm
*Lactobacillus acidophilus*—0.51 gm (From $1.44 \times 10^{11}$)
*Lactobacillus plantarum*—0.55 gm (From $2.38 \times 10^{11}$)
Temperature: 180° C.
Baking Time: 12 minutes Method of Preparation:
1. The probiotics (*Lactobacillus acidophilus/Lactobacillus plantarum*) powder is suspended in 0.9% NaCl overnight (15-17 hours)
2. The dry ingredients (All-purpose flour, salt, baking powder are then weighed and mixed thoroughly for 5-10 minutes.
3. Then butter is taken in a beaker & granulated sugar is added and beaten till it becomes fluffy after approximately 2-3 minutes.
4. Then to this the overnight probiotic solution (*Lactobacillus acidophilus/Lactobacillus plantarum*) pre-weighed as per requirement (5.0 billion cfu/cookie) is added and is mixed uniformly.
5. To this vanilla extract & milk is added and then all the ingredients are whisked together for 5-10 minutes.
6. Then the cookie dough is flattered on a parchment paper & chilled in refrigerator (4-8° C.) for 1 hour
7. After 1 hour, the oven is kept for pre-heating and the cookie dough is baked at 180.0 for 12 minutes.
8. After baking for 12 minutes the cookie is cooled for 5-10 minutes at room temperature.
9. Then the cookie is taken up for total viable count analysis to check the viability of probiotic.

Example 3: Heat Stability of Thermostable Strains

Example 3A

The stability of the heat stable probiotic strain *Lactobacillus plantarum* is determined in this example.
The stability of *Lactobacillus plantarum* at 90° C., 140° C. &160° C. is checked for different time intervals in a Hot Air Oven. The results are depicted in the table below.

TABLE 2A

| Sl No. | Time Interval | TVSC (billion/g) | % of Viability |
| --- | --- | --- | --- |
| | Initial assay | 6.20 | 100% |
| 1 | 90° C. for 30 sec | 6.10 | 98.3% |
| 2 | 90° C. for 60 sec | 6.02 | 97.0% |
| 3 | 90° C. for 120 sec | 5.90 | 95.1% |

Figure 4A:
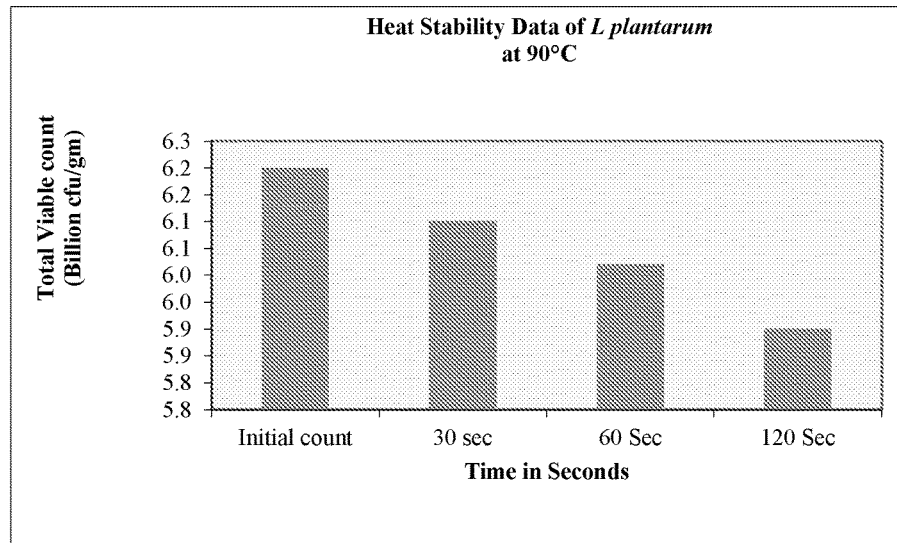
FIGS. 4A, 4B and 4C depict the stability of thermostable strain Lactobacillus plantarum TSP-Lp1 at 90° C., 140° C. and 160° C.

It is derived from the table above and FIG. 4A of the present disclosure that the *Lactobacillus plantarum* is 95% viable at 90° C. for 120 seconds.

TABLE 2B

| Sl No. | Time Interval | TVSC (billion/g) | % of Viability |
| --- | --- | --- | --- |
| | Initial assay | 6.20 | 100% |
| 1 | 140° C. for 30 sec | 6.10 | 98.3% |
| 2 | 140° C. for 60 sec | 5.8 | 93.5% |
| 3 | 140° C. for 120 sec | 5.5 | 88.7% |

Figure 4B:
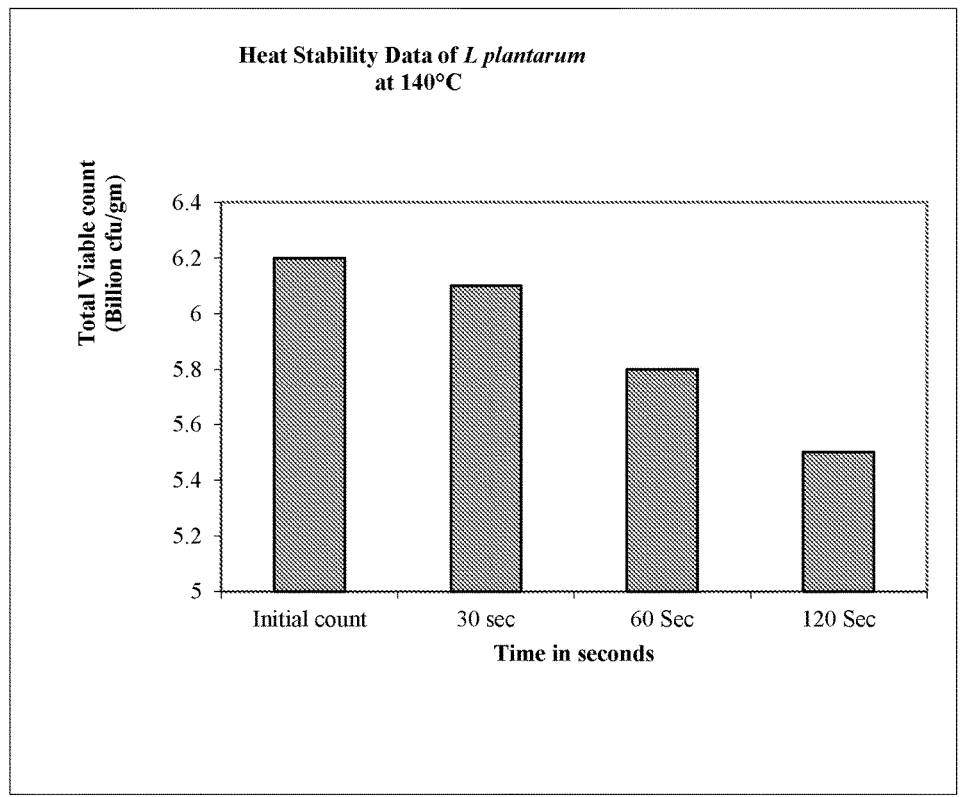

It is derived from the table above and FIG. 4B of the present disclosure that *Lactobacillus plantarum* is 88% viable at 140° C. for 120 seconds.

TABLE 2C

| Sl No. | Time Interval | TVSC (billion/g) | % of Viability |
| --- | --- | --- | --- |
| | Initial assay | 6.20 | 100% |
| 1 | 160° C. for 2 min | 3.20 | 52.4% |

TABLE 2C-continued

| Sl No. | Time Interval | TVSC (billion/g) | % of Viability |
|---|---|---|---|
| 2 | 160° C. for 5 min | 0.68 million | 11.0% |
| 3 | 160° C. for 10 min | 0.0% | 0.00% |

Figure 4C:
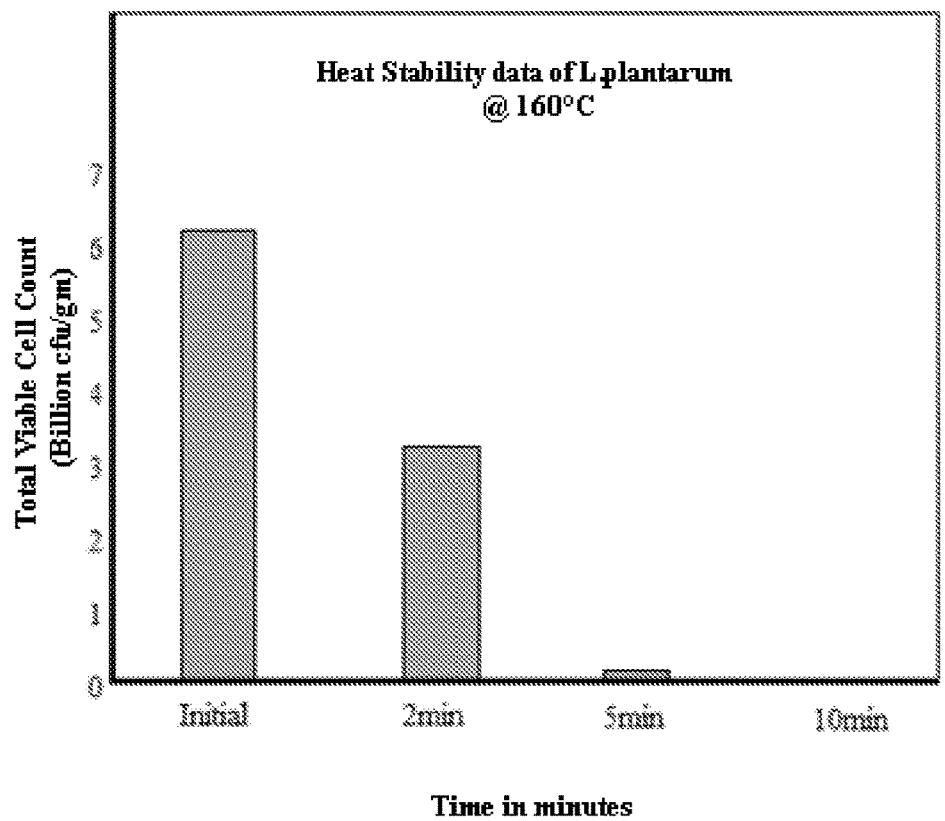

It is derived from the table above and FIG. 4C of the present disclosure that *Lactobacillus plantarum* is still 11% viable at 160° C. for 300 seconds.

Example 3B

The stability of the heat stable probiotic strain *Lactobacillus acidophilus* TSP-La-1 is determined in this example.
The stability of *Lactobacillus acidophilus* at 90° C., 140° C. &160° C. is checked for different time intervals in a Hot Air Oven. The results are depicted in the table below.

TABLE 2D

| Sl No. | Time Interval | TVCC (billion cfu/gm) | % of Viability |
|---|---|---|---|
| | Initial assay | 2.16 | 100% |
| 1 | 90° C. for 30 sec | 2.10 | 97.2% |
| 2 | 90° C. for 60 sec | 1.98 | 91.6% |
| 3 | 90° C. for 120 sec | 1.75 | 81.0% |

Figure 4D:
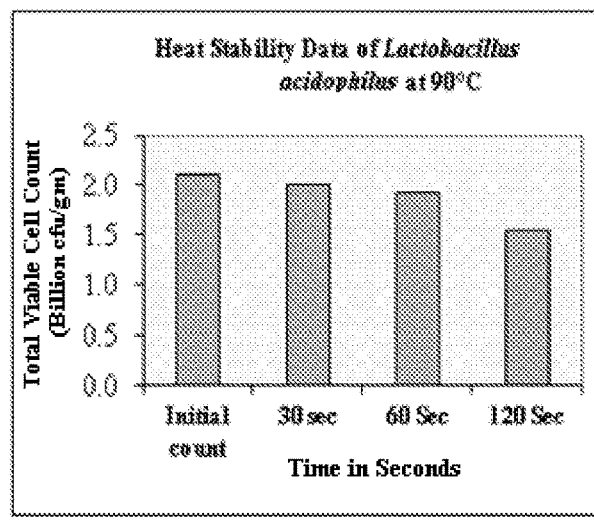
FIGS. 4D, 4E and 4F depict the stability of thermostable strain Lactobacillus acidophilus TSP-La1 at 90° C., 140° C. and 160° C.

Conclusion:
The above data and FIG. 4D shows that *Lactobacillus acidophilus* is still heat stable and viable at 81% at 90° C. for 120 sec.

TABLE 2E

| Sl No. | Time Interval | TVCC (billion cfu/g) | % of Viability |
|---|---|---|---|
| | Initial assay | 2.16 | 100% |
| 1 | 140° C. for 30 sec | 2.08 | 96.2% |
| 2 | 140° C. for 60 sec | 1.90 | 89.3% |
| 3 | 140° C. for 120 sec | 1.55 | 71.7% |

Figure 4E:
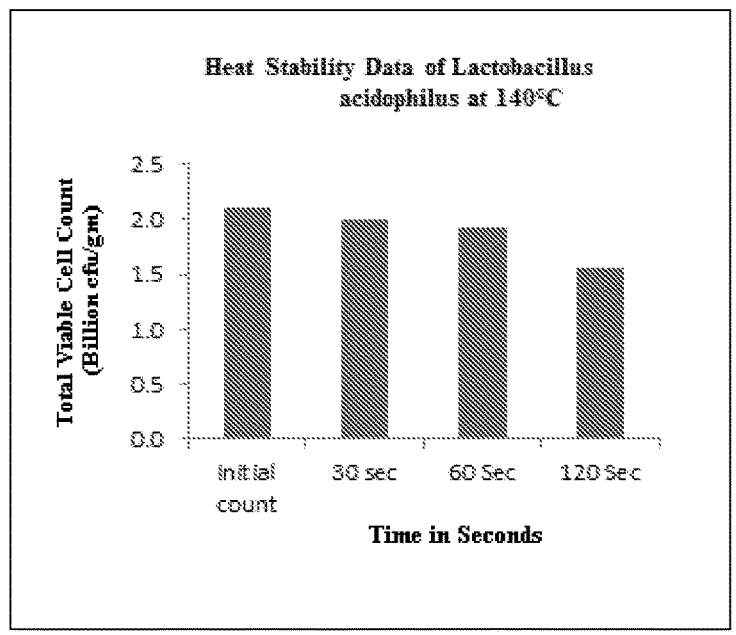

Conclusion:
The above data and FIG. 4E shows that *Lactobacillus acidophilus* is still heat stable and viable at 71% at 140° C. for 120 sec.

TABLE 2F

| Sl No. | Time Interval | TVCC (billion cfu/gm) | % of Viability |
|---|---|---|---|
| | Initial assay | 2.1 | 100% |
| 1 | 160° C. for 2 min | 0.86 | 4.09% |
| 2 | 160° C. for 5 min | 0.0 | 0.0% |
| 3 | 160° C. for 10 min | 0.0 | 0.0% |

Figure 4F:
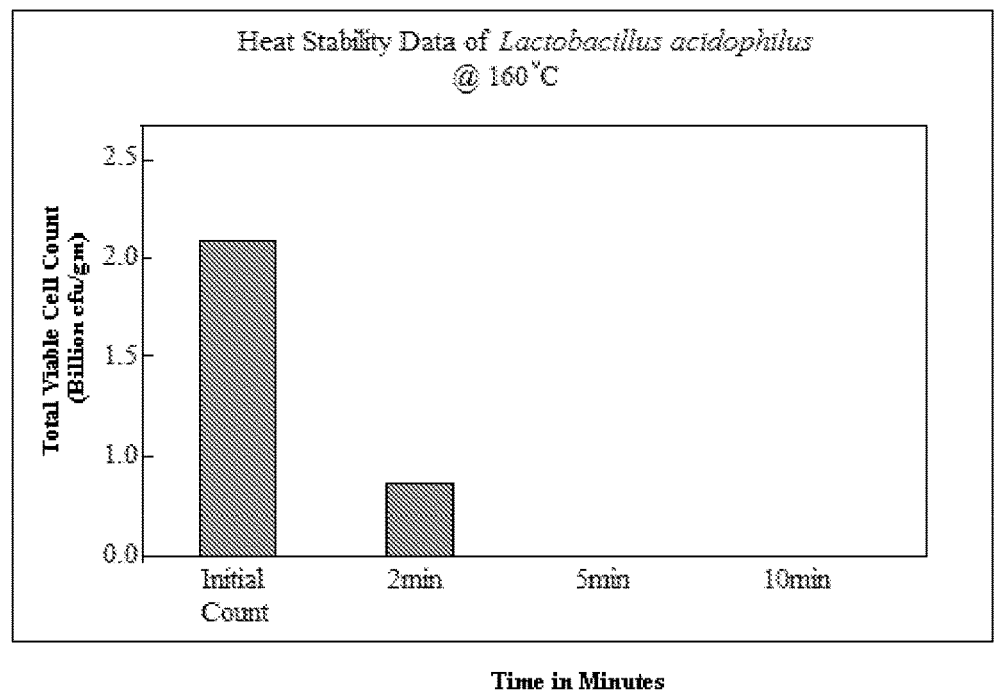

Conclusion:
The above data and FIG. 4F shows that *Lactobacillus acidophilus* 4.09% is still Heat stable at 160° C. for 120 sec Example 3C During the preparation of Probiotic gummies, chocolates and soup, the probiotic strains are subjected to high temperatures where the probiotic strains are present/added. The heat stability exhibited by these probiotic strains in the food products are determined by checking their viability.

Figure 2A:
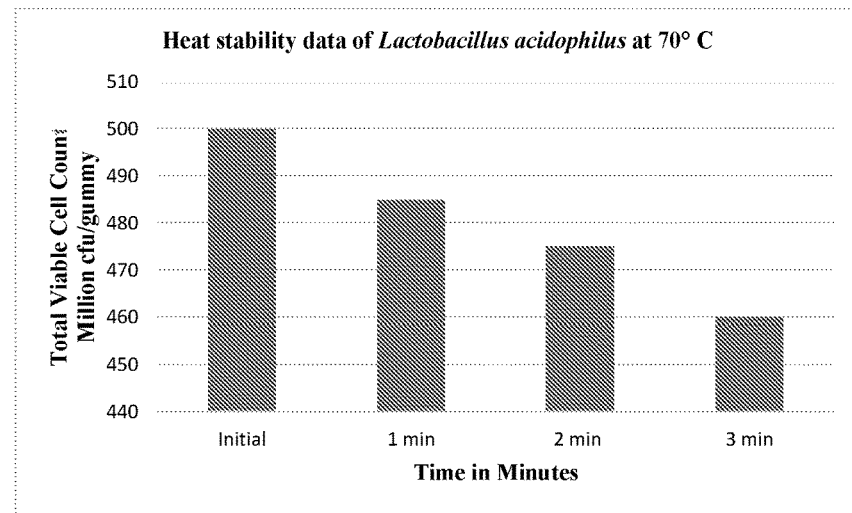
FIG. 2A depicts the stability of thermostable strain Lactobacillus acidophilus (TSP-La1) at 70° C. for different time intervals in gummies.

As shown in Table 3A below and FIG. 2A, it is observed that in Gummies, *Lactobacillus acidophilus* is 92.0% viable at 70° C. for time duration up to 3 minutes.

TABLE 3A

| Sl No. | Time Interval | TVCC (Million cfu/gummy) | % of Viability |
|---|---|---|---|
| | Initial Assay | 500 | 100% |
| 1 | 70° C. for 1 min | 485 | 97% |
| 2 | 70° C. for 2 minutes | 475 | 95% |
| 3 | 70° C. for 3 minutes | 460 | 92% |

Figure 2B:
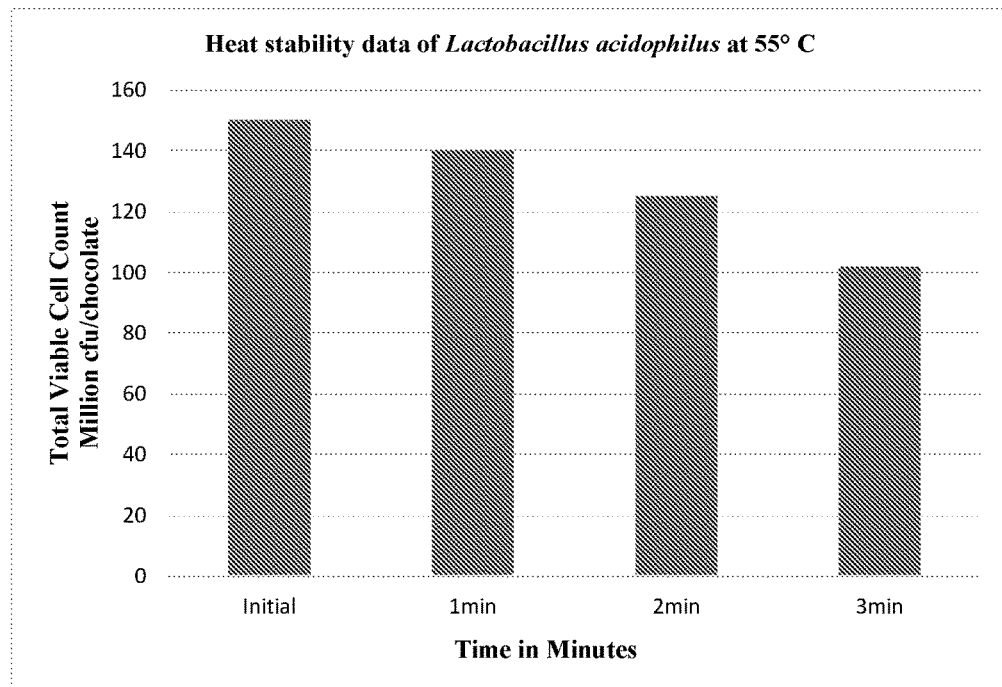
FIG. 2B depicts the stability of thermostable strain Lactobacillus acidophilus (TSP-La1) at 55° C. for different time intervals in chocolates.

As shown in Table 3B below and FIG. 2B, it is observed that in chocolates, *Lactobacillus acidophilus* is 83.3% viable at 55° C. for time duration up to 2 minutes.

TABLE 3B

| Sl No. | Time Interval | TVCC (Million cfu/chocolate) | % of Viability |
|---|---|---|---|
| | Initial Assay | 150 | 100% |
| 1 | 55° C. for 1 min | 140 | 93.3% |
| 2 | 55° C. for 2 minutes | 125 | 83.3% |
| 3 | 55° C. for 3 minutes | 102 | 68.0% |

The above results depict that the *Lactobacillus acidophilus* is stable up to 83% and viable at 55° C. for up to 2 minutes and is 68.0% viable at 55° C. up to 3 minutes.

Figure 3:
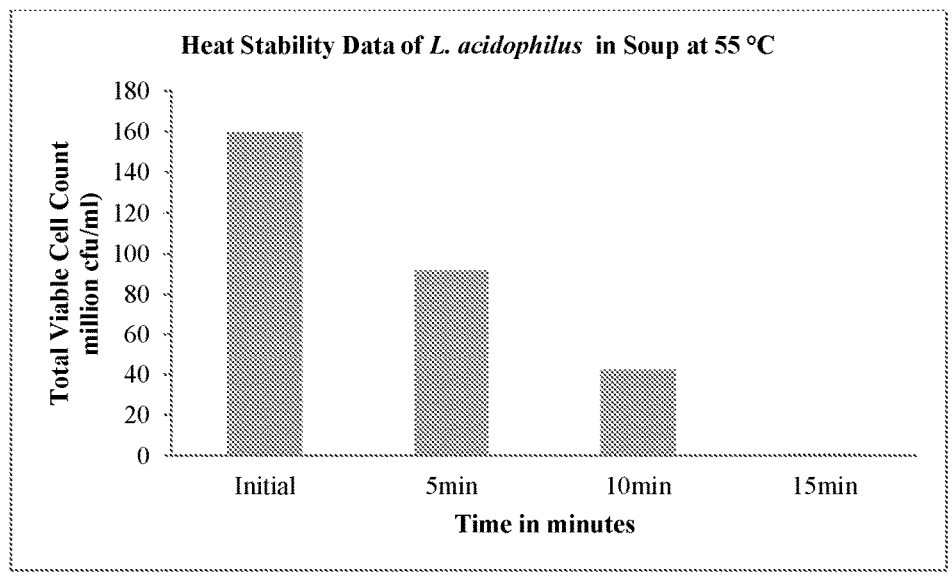
FIG. 3 depicts the stability of thermostable strain Lactobacillus acidophilus TSP-La1 at 55° C. for initial period and after 10 minutes in soup.

As shown in Table 3C below and FIG. 3, it is observed that in soup (liquid medium), *Lactobacillus acidophilus*, is 57% viable at 55° C. for 5 minutes & 26% viable up to 10 minutes.

TABLE 3C

| Sl No. | Time Interval | TVCC (Million cfu/ml) | % of Viability |
|---|---|---|---|
| | Initial Assay | 160 | 100% |
| 1 | 55° C. for 5 min | 91.6/ml | 57.2 |
| 2 | 55° C. for 10 minutes | 42.3/ml | 26.4 |
| 3 | 55° C. for 15 minutes | 0.94/ml | 0.59 |

The same experiment as above is performed by introducing *Lactobacillus plantarum* strains into soup and checking the viability at 55° C. and 75° C., where the viability is found to be good, as shown in Table 3D.

TABLE 3D

| Sl No. | Time Interval | TVCC (Million cfu/ml) | % of Viability |
|---|---|---|---|
| | Initial Assay | 160 | 100% |
| 1 | 55° C. for 5 min | 7.8 | 4.87% |
| 2 | 55° C. for 10 minutes | 3.7 | 2.31% |
| 3 | 55° C. for 15 minutes | 0.27 | 0.16% |

Example 3D

*Lactobacillus plantarum* (TSP-Lp1) strain and *Lactobacillus acidophilus* TSP-La1 strain is incorporated into cookie dough, cookies are baked and their stability is checked at 180° C. The results are provided in Tables 4A and 4B below.

TABLE 4A

*Lactobacillus acidophilus* TSP-La1

| Time Interval | TVCC (Billion/cookie) | % of Viability |
|---|---|---|
| Intial assay | 5.0 | 100% |
| 1  180° C. for 12 min | 2.76 | 55% |

TABLE 4B

*Lactobacillus plantarum* (TSP-Lp1)

| Time Interval | TVCC (Billion/cookie) | % of Viability |
|---|---|---|
| Intial Assay | 5.0 | 100% |
| 1  180° C. for 12 min | 1.85 | 37% |

Figure 12A:
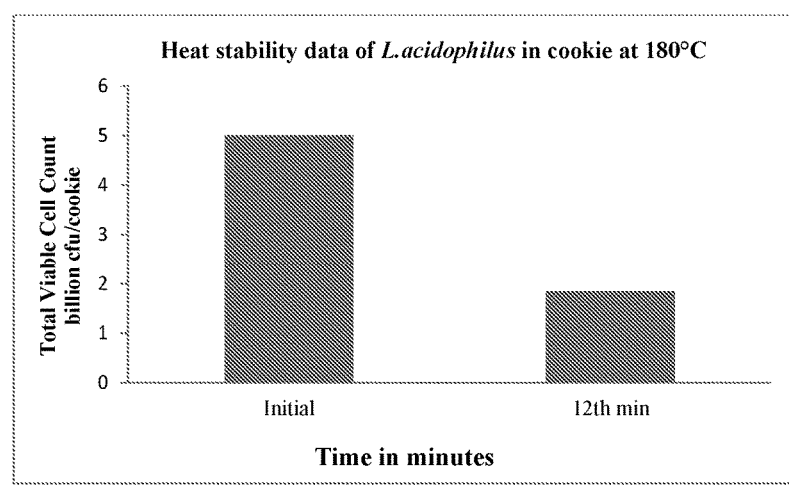
FIGS. 12A and 12B depict stability of Lactobacillus acidophilus TSP-La1 and Lactobacillus plantarum TSP-Lp1 in cookie at 180° C. for 12 minutes.
Figure 12B:
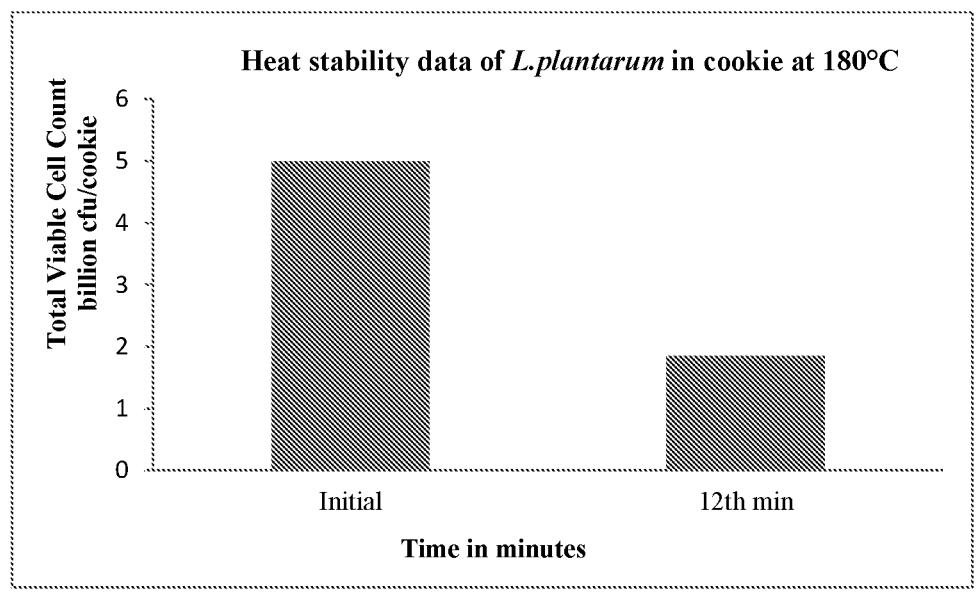

It is derived from Tables 4A and 4B, and FIGS. 12A and 12B that *Lactobacillus acidophilus* is 55% viable at 180° C. for 12 minutes and *Lactobacillus plantarum* is 37% viable at 180° C. for 12 minutes.

Example 4: Heat Stability of Thermostable Strains in Muffins Food Product

The probiotic muffins are prepared by adding the *Lactobacillus acidophilus* TSP-La1 and *Lactobacillus plantarum* TSP-Lp1 strains to them during their preparation. The muffins are baked in an oven at 160° C. for 15 minutes.

TABLE 5A

| Time Interval | TVCC (Billion cfu/muffin) | % of Viability |
|---|---|---|
| Initial assay | 10.0 | 100% |
| 1  160° C. for 15 min | 7.5 | 75% |

TABLE 5B

| Time Interval | TVSC (Billion cfu/muffin) | % of Viability |
|---|---|---|
| Initial assay | 5.0 | 100% |
| 1  160° C. for 15 min | 3.85 | 77% |

Figure 5A:
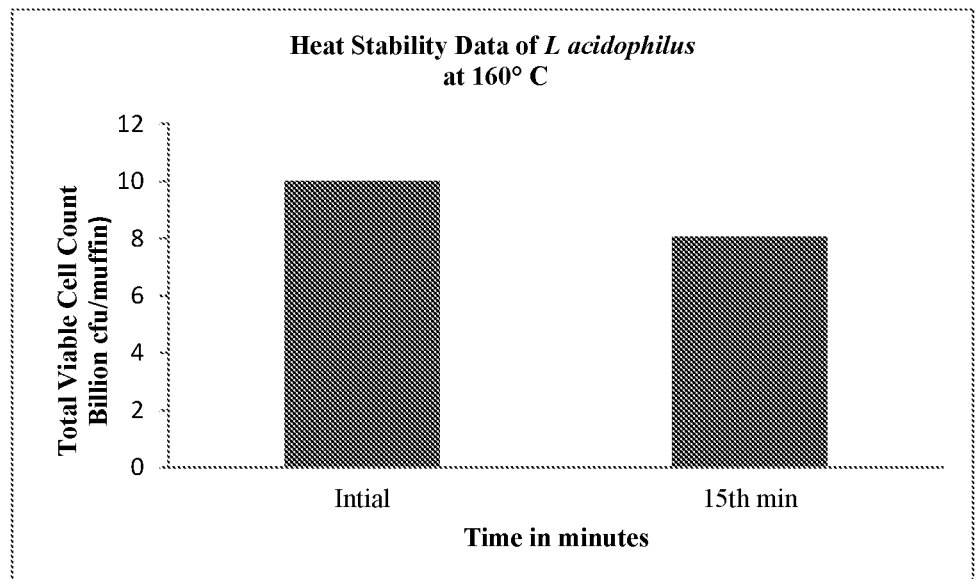
FIGS. 5A and 5B depicts the stability of thermostable strain Lactobacillus acidophilus TSP-La1 and Lactobacillus plantarum TSP-Lp1 at 160° C. for initial period and after 15 minutes in muffins.
Figure 5B:
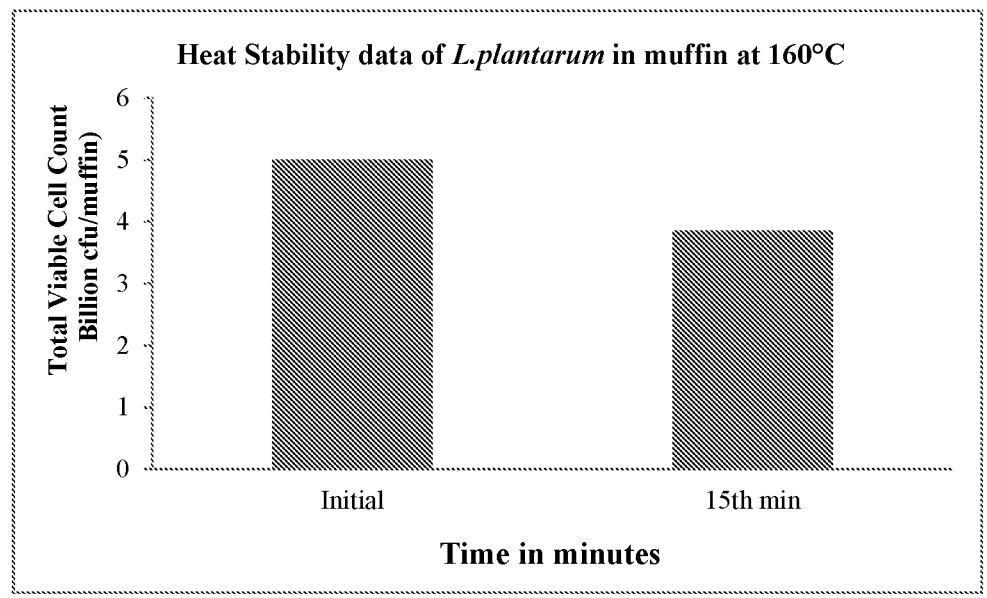

It is observed from Tables 5A-5B and FIGS. 5A-5B that the thermostable strain *Lactobacillus acidophilus* in the muffin depicts a viability of up to 75% at 160.0 for 15 minutes. Further, *Lactobacillus plantarum* is 77% viable at 160° C. for 15 minutes.

Example 5A: Heat Stability of *Lactobacillus acidophilus* in Bread Food Product

This study is conducted to check the stability of *Lactobacillus acidophilus* in bread which is baked in oven at temperatures above 200° C. The Table No. 6 as depicted below showcases that the *Lactobacillus acidophilus* strains of the present disclosure are stable at temperatures as high as 240° C. for a period of about 10 minutes.

TABLE 6

| Time Interval | TVCC (Billion cfu/bread) | % of Viability |
|---|---|---|
| Initial assay | 5.0 | 100% |
| 1  240° C. for 10 min | 3.0 | 60% |

Thus, it is clear that the *Lactobacillus acidophilus* strains of the present disclosure are stable in extremely high temperatures like 240° C. with a viability of 60% and thereby provide for efficient heat stable strains.

Figure 6:
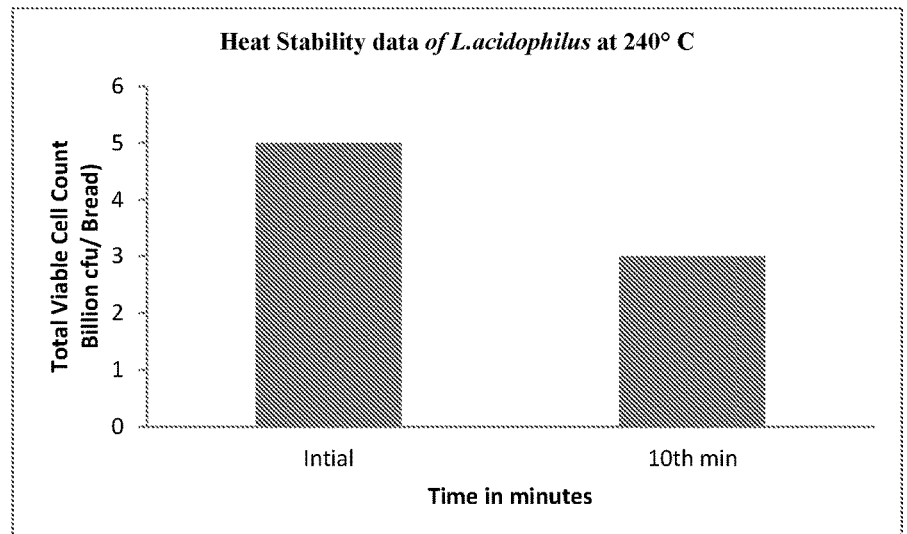
FIG. 6 depicts the stability of thermostable strain Lactobacillus acidophilus TSP-La1 at 240° C. for initial period and after 10 minutes in bread.

The above data in the table and FIG. 6 shows that *Lactobacillus acidophilus* is 60% viable at 240° C. for 10 minutes.

Example 5B: Heat Stability of *Lactobacillus plantarum* in Bread Food Product

This study is conducted to check the stability of *Lactobacillus plantarum* in bread which is baked in oven at temperatures above 200° C. This study showcases that the *Lactobacillus plantarum* strains of the present disclosure are stable at temperatures as high as 240° C. for a period of about 10 minutes.

TABLE 7

| Time Interval | TVCC (Billion/bread) | % of Viability |
|---|---|---|
| Initial assay | 5.0 | 100% |
| 1  240° C. for 10 min | 0.5 | 10% |

Example 6A: Heat Stability of *Lactobacillus acidophilus* in Tea at 50° C. and 60° C. for Different Time Intervals It is stated in the prior art that *Lactobacillus* species are not viable in liquid medium. However, when the *Lactobacillus acidophilus* TSP-La1 of the present disclosure is formulated into a tea product (Twining's Tea), which is later suspended in water while brewing the tea, significant amount of viability of about 39% is observed at 50° C. and 60° C. for up to 7 minutes.

TABLE 8A

| Sl No. | Time Interval | TVCC (million cfu/tea bag) | % of Viability |
|---|---|---|---|
|  | Initial Count | 100 million | 100% |
| 1 | 50° C. for 1 min | 65.6 million | 65.6% |
| 2 | 50° C. for 3 min | 50.0 million | 50.0% |
| 3 | 50° C. for 5 min | 48.0 million | 48.0% |
| 4 | 50° C. for 7 min | 39.0 million | 39.0% |
| 5 | 50° C. for 10 min | 1.0 million | 1.0% |

TABLE 8B

| Sl No. | Time Interval | TVCC (million cfu/tea bag) | % of Viability |
|---|---|---|---|
|  | Initial Count | 100 million | 100% |
| 1 | 60° C. for 1 min | 43.0 million | 43.0% |
| 2 | 60° C. for 3 min | 28.36 million | 28.36% |
| 3 | 60° C. for 5 min | 25.60 million | 25.60% |
| 4 | 60° C. for 7 min | 1.41 million | 1.41% |
| 5 | 60° C. for 10 min | 0.84 million | 0.84% |

Figure 7A:
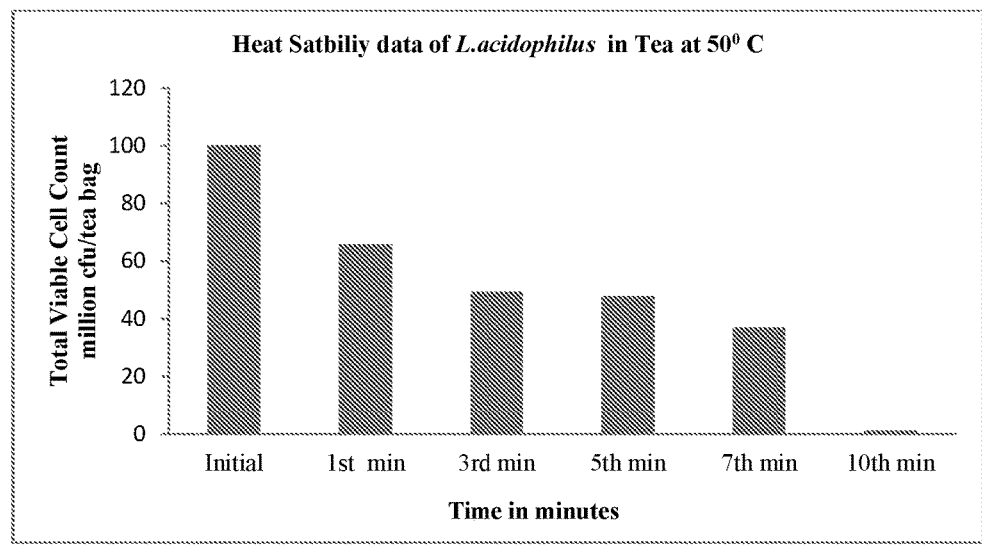
FIGS. 7A and 7B depict the viability of thermostable strain Lactobacillus acidophilus TSP-La1 in Twining's Tea sample at 50° C. and 60° C. respectively for varied time period.
Figure 7B:
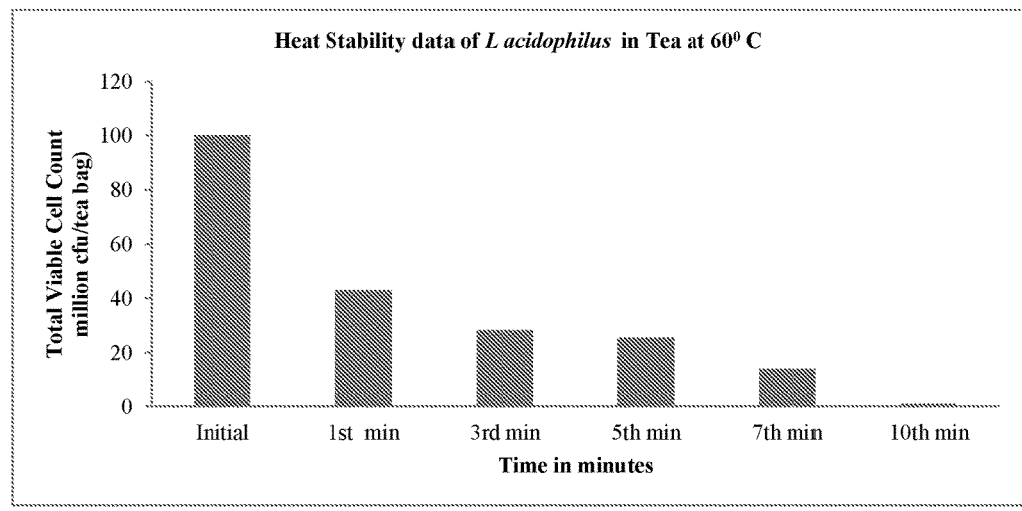

From the above data in the tables and from FIGS. 7A and 7B, it is inferred that the LA strains of the present disclosure are viable in liquid medium at room temperature and higher temperatures like 50° C. and 60° C. and hence these strains can be formulated into even liquid based media/product.

Example 6B: Heat Stability of *Lactobacillus plantarum* in Tea at 50° C. and 60° C. for Different Time Intervals It is stated in the prior art that *Lactobacillus* species are not viable in liquid medium. However, when the *Lactobacillus plantarum* TSP-Lp1 of the present disclosure is formulated into a tea product (Twining's Tea), which is later suspended in water while brewing the tea, significant amount of viability is observed at 50° C. and 60° C.

TABLE 9A

| Sl No. | Time Interval | TVCC (million cfu/tea bags) | % of Viability |
|---|---|---|---|
|  | Initial Count | 100 million | 100% |
| 1 | 60° C. for 1 min | 29.0 million | 29.0% |
| 2 | 60° C. for 3 min | 26.0 million | 26.0% |
| 3 | 60° C. for 5 min | 4.1 million | 4.1% |
| 4 | 60° C. for 7 min | 0.0 million | 0.0% |
| 5 | 60° C. for 10 min | 0.0 million | 0.0% |

TABLE 9B

| Sl No. | Time Interval | TVCC (million cfu/tea bags) | % of Viability |
|---|---|---|---|
|  | Initial Count | 100 million | 100% |
| 1 | 60° C. for 1 min | 17.5 million | 17.5% |
| 2 | 60° C. for 3 min | 2.75 million | 2.75% |
| 3 | 60° C. for 5 min | 0.0036 million | 0.0036% |
| 4 | 60° C. for 7 min | 0.0 million | 0.0% |
| 5 | 60° C. for 10 min | 0.0 million | 0.0% |

Example 7: Acid Tolerance of *Lactobacillus acidophilus* at Different pH and Time Intervals The *Lactobacillus acidophilus* strains are subjected to extreme pH conditions within the range of 1.5 to 3.0 to ascertain that the food products containing these strains are able to survive the low acidity of the stomach during digestion. Total plate counts for *Lactobacillus acidophilus* on GYEA agars at different pH values of 1.5, 3.0 and 7.2 (control) over 1.5 hour intervals. The table no. 10 below depicts the plate viability of LA strains when subjected to pH 1.5, 2.5 3.0 and 7.2 for 0.5, 1.5 and 3 hours. The period of 0 hour is the time when the cultures are plated immediately for assay upon being exposed to PBS with different pH values.

TABLE 10

| | | Total plate counts ($\log_9$ CFU/mL) | | | | | |
|---|---|---|---|---|---|---|---|
| Strain | pH | 0 hr | % of Viability | 1.5 hr | % of Viability | 3.0 hr | % of Viability |
| *Lactobacillus acidophilus* TSP La-1(TPPL-ACDHS100) | 1.5 | 0.39 | 32.23% | — | 0.0% | — | 0.0% |
| | 3.0 | 0.99 | 81.61% | 0.95 | 78.5% | 0.92 | 76.03% |
| | 7.2 | 1.21 | 100% | 1.05 | 86.77% | 1.0 | 82.64% |

Figure 8:
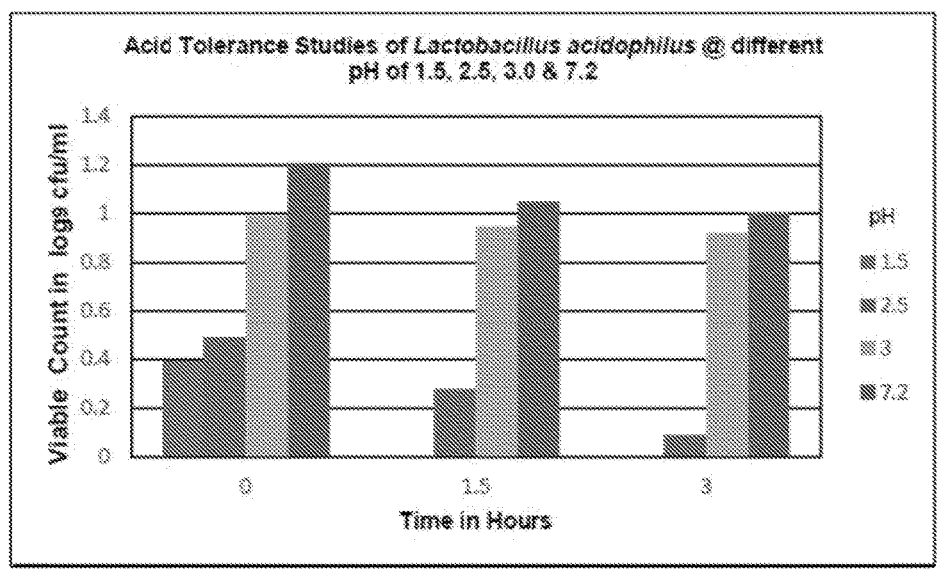
FIG. 8 depicts the Acid tolerance quantitative analysis for thermostable strain Lactobacillus acidophilus TSP-La1 at different pH.

It is observed from the table above and FIG. 8 that the strains are able to resist the low pH of the stomach and are viable in the stomach. At pH 3.0, the *Lactobacillus acidophilus* has steady viability until 3.0 hour.

Thus, the thermo-stable strains of the present disclosure are suitable for being incorporated into food products and act beneficially in the environment of the stomach.

Example 8: Acid Tolerance of *Lactobacillus plantarum* at Different pH and Time Intervals The same acid tolerance test as provided in Example 7 is conducted with *Lactobacillus plantarum* TSP-Lp1 and similar results are observed. The table no. 11 below indicates the viability % of the LP strains subjected to the low pH usually present in the stomach. The period of 0 hour is the time when the cultures are plated immediately for assay upon being exposed to PBS with different pH value.

TABLE 11

| | | Total plate counts ($\log_9$ CFU/mL) | | | | | |
|---|---|---|---|---|---|---|---|
| Strain | pH | 0 hr | % of Viability | 1.5 hr | % of Viability | 3.0 hr | % of Viability |
| *Lactobacillus plantarum* | 1.5 | 0.76 | 47.20% | — | 0.0% | 0.0 | 0.0% |
| | 2.5 | 0.84 | 52.17% | 0.19 | 11.8% | 8 cfu/ml | 0.004% |

TABLE 11-continued

| Strain | pH | 0 hr | % of Viability | 1.5 hr | % of Viability | 3.0 hr | % of Viability |
|---|---|---|---|---|---|---|---|
| TSP-Lp1 | 3.0 | 1.20 | 74.50% | 0.58 | 36.02% | 0.11 | 6.83% |
|  | 7.2 | 1.61 | 100% | 1.20 | 74.50% | 1.03 | 63.90% |

Figure 9:
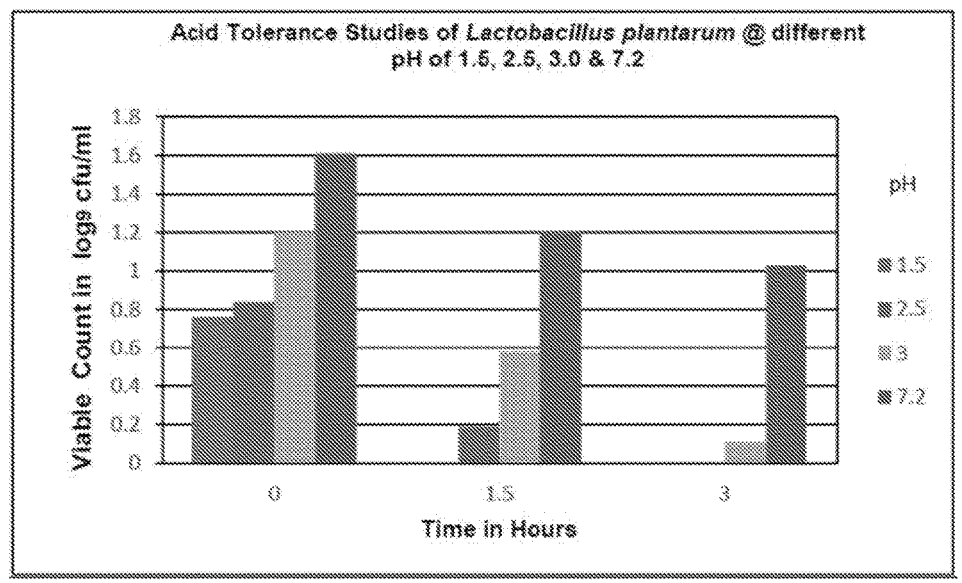
FIG. 9 depicts the Acid tolerance quantitative analysis for Lactobacillus plantarum TSP-Lp1 at different pH.

From the above results in the table and FIG. 9, it is evident that the LP strains of the present disclosure are viable at low pH for a considerable amount of time. At pH 3.0, the *Lactobacillus plantarum* has steady viability until 3.0 hours.

Thus, the thermo-stable strains of the present disclosure are suitable for being incorporated into food products and act beneficially in the environment of the stomach.

Example 9: Antibiotic Susceptibility Profiles of *Lactobacillus acidophilus* by the Disk Diffusion Method In order to ascertain the sensitivity of the thermostable strains in the food products towards antibiotics, Antibiotic susceptibility profile for *Lactobacillus acidophilus* is created by disk diffusion method. The susceptibility criteria used is established by Charteris et al. The *Lactobacillus acidophilus* is grown in Man Rogosa Sharpe Agar (MRSA).

*Lactobacillus* MRS Agar M641—Method of Preparation
*Lactobacillus* MRS Agar is recommended for cultivation of all *Lactobacillus* species.

Composition

| Ingredients | Gms/Litre |
|---|---|
| Proteose peptone | 10.000 |
| Beef extract | 10.000 |
| Yeast extract | 5.000 |
| Dextrose | 20.000 |
| Poly sorbate 80 | 1.000 |
| Ammonium citrate | 2.000 |
| Sodium acetate | 5.000 |
| Magnesium sulphate | 0.100 |
| Manganese sulphate | 0.050 |
| Di potassium phosphate | 2.000 |
| Agar | 12.000 |
| Final pH (at 25° C.) | 6.5 ± 0.2 |

67.15 grams is suspended in 1000 ml distilled water and heated to boiling to dissolve the medium completely. It is sterilized by autoclaving at 15 lbs pressure (121° C.) for 20 minutes, mixed well and poured into sterile Petri plates.

The table below depicts the results carried out for a list of common antibiotics. The concentration of the tested antibiotics has been included depending upon their minimum inhibitory concentrations.

TABLE 12

| Sl No | Antibiotic | Concentration | MIC Results | Resistant/Sensitive |
|---|---|---|---|---|
| STRAIN: *Lactobacillus acidophilus* TSP-La1 | | | | |
| 01. | Ampicillin | 10 µg | 10 mm | Resistant |
| 02. | Amoxicillin | 30 µg | 32 mm | Sensitive |
| 03. | Ciprofloxacin | 10 µg | 22 mm | Sensitive |
| 04. | Cephalothin | 30 µg | 25 mm | Sensitive |
| 05. | Chloramphenicol | 30 µg | 29 mm | Sensitive |
| 06. | Clindamycin | 2 µg | 31 mm | Sensitive |

TABLE 12-continued

| Sl No | Antibiotic | Concentration | MIC Results | Resistant/Sensitive |
|---|---|---|---|---|
| 07. | Erythromycin | 15 µg | 14 mm | Resistant |
| 08. | Gentamycin | 10 µg | 10 mm | Resistant |
| 09. | Kanamycin | 30 µg | No Zone | Resistant |
| 10. | Methicillin | 5 µg | 30 mm | Sensitive |
| 11. | Oxacillin | 1 µg | No Zone | Resistant |
| 12. | Rifampicin | 5 µg | 35 mm | Sensitive |
| 13. | Streptomycin | 10 µg | 18 mm | Sensitive |
| 14. | Tetracycline | 30 µg | 11 mm | Resistant |
| 15. | Vancomycin | 30 µg | No Zone | Resistant |

It is seen from the table above that the *Lactobacillus acidophilus* strain of the present disclosure is sensitive to Amoxicillin, Ciprofloxacin, Cephalothin, Chloramphenicol, Clindamycin, Methicillin, Rifampicin and Streptomycin and is resistant to Ampicillin, Erythromycin, Gentamycin, Kanamycin, Oxacillin, Tetracycline and Vancomycin.

Example 10: Antibiotic Susceptibility Profiles of *Lactobacillus plantarum* by the Disk Diffusion Method The same set of study as the previous example is conducted using *Lactobacillus plantarum* strain of the present disclosure and the results for the study are depicted in Table No. 13 as below. The susceptibility criteria used is established by Charteris et al. The *Lactobacillus acidophilus* is grown in Man Rogosa Sharpe Agar,

TABLE 13

| Sl No | Antibiotic | Concentration | MIC Results | Resistant/Sensitive |
|---|---|---|---|---|
| STRAIN: *Lactobacillus plantarum* TSP-Lp1 | | | | |
| 01. | Ampicillin | 10 µg | No Zone | Resistant |
| 02. | Amoxicillin | 30 µg | 39 mm | Sensitive |
| 03. | Ciprofloxacin | 10 µg | 31 mm | Sensitive |
| 04. | Cephalothin | 30 µg | 23 mm | Sensitive |
| 05. | Chloramphenicol | 30 µg | 31 mm | Sensitive |
| 06. | Clindamycin | 2 µg | 34 mm | Sensitive |
| 07. | Erythromycin | 15 µg | 14 mm | Sensitive |
| 08. | Gentamycin | 10 µg | 8 mm | Resistant |
| 09. | Kanamycin | 30 µg | No Zone | Resistant |
| 10. | Methicillin | 5 µg | 15 mm | Sensitive |
| 11. | Oxacillin | 1 µg | No Zone | Resistant |
| 12. | Rifampicin | 5 µg | 43 mm | Sensitive |
| 13. | Streptomycin | 10 µg | 20 mm | Sensitive |
| 14. | Tetracycline | 30 µg | 14 mm | Sensitive |
| 15. | Vancomycin | 30 µg | No Zone | Resistant |

From the above table, it is observed that *Lactobacillus plantarum* is sensitive to Amoxicillin, Ciprofloxacin, Cephalothin, Chloramphenicol, Clindamycin, Erythromycin, Methicillin, Rifampicin, Streptomycin and Tetracycline and resistant to Ampicillin, Gentamycin, Kanamycin, Oxacillin and Vancomycin.

Example 11: Bile Tolerance of *Lactobacillus acidophilus* at Different Bile Concentration Values and Time Intervals The strains of *Lactobacillus acidophilus* TSP-La1 thermostable strain of the present disclosure are tested for their tolerance towards various concentrations to Bile in the body. Therefore, various concentrations of Bile ranging from 0.3% to 1% are subjected to the LA strains of the present disclosure as depicted in Table no. 14 below.

Total plate counts for *Lactobacillus acidophilus* on GYEA agars at different bile concentration of 0.3%, 0.5%, 1.0% and control over 0, 3.0 and 6.0 hour intervals are provided in the table below. The period of 0 hour is the time when the cultures are plated immediately for assay upon being exposed to PBS with different Bile concentration values.

It is to be noted that the concentration for Bile in the body only reaches up to a maximum of 1%.

TABLE 14

| | | Total plate counts ($\log_9$ CFU/mL) | | | | | |
|---|---|---|---|---|---|---|---|
| Strain | Bile Conc., | 0 hr | % of Viability | 3.0 hr | % of Viability | 6.0 hr | % of Viability |
| Lactobacillus | 0.3% | 1.37 | 94.4% | 1.29 | 82.69% | 0.75 | 44.6% |
| acidophilus | 0.5% | 1.18 | 81.3% | 1.02 | 65.38% | 0.59 | 35.1% |
| TSP-La1 | 1.0% | 1.05 | 72.4% | 0.12 | 7.69% | 0.02 | 1.19% |
| | Control | 1.45 | 100% | 1.56 | 100% | 1.68 | 100% |

Figure 10:
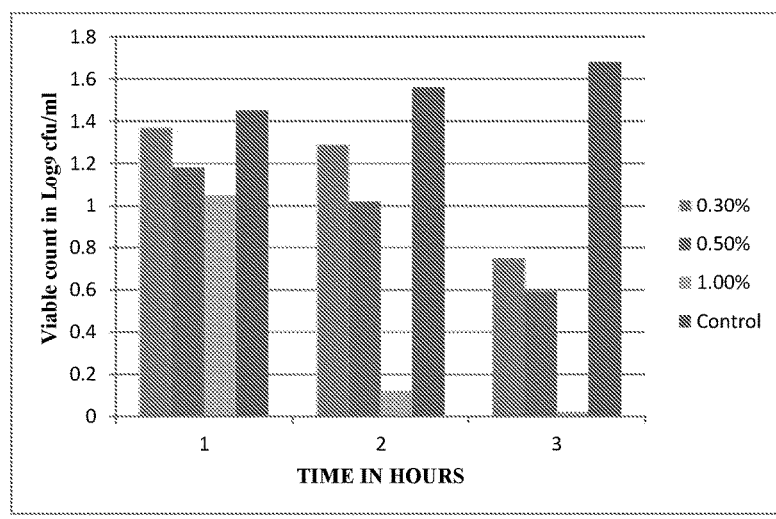
FIG. 10 depicts the Bile Tolerance of thermostable strain Lactobacillus acidophilus TSP-La1 at different bile concentration values and time intervals.

From the above table and FIG. 10 of the present disclosure, it is clear that the LA strains of the present disclosure are capable of tolerating high concentrations of the Bile. Thus, the thermo-stable strains of the present disclosure are suitable for being incorporated into food products and act beneficially in the environment of the stomach.

Example 12: Bile Tolerance of *Lactobacillus plantarum* at Different Bile Concentration and Time Intervals The same study as described in the previous example is carried out with *Lactobacillus plantarum* TSP-Lp1 strain of the present disclosure, wherein the strain is subjected to different concentrations of Bile i.e. 0.3% to 1%.

The table below provides the viability % of the LP strains of the present disclosure when subjected to varying concentrations of Bile. Total plate counts for *Lactobacillus plantarum* on GYEA agars at different bile concentration of 0.3%, 0.5%, 1.0% and control aver 0, 3.0 and 6.0 hour intervals are provided. The period of 0 hour is the time when the cultures are plated immediately for assay upon being exposed to PBS with different Bile concentration values.

Figure 11:
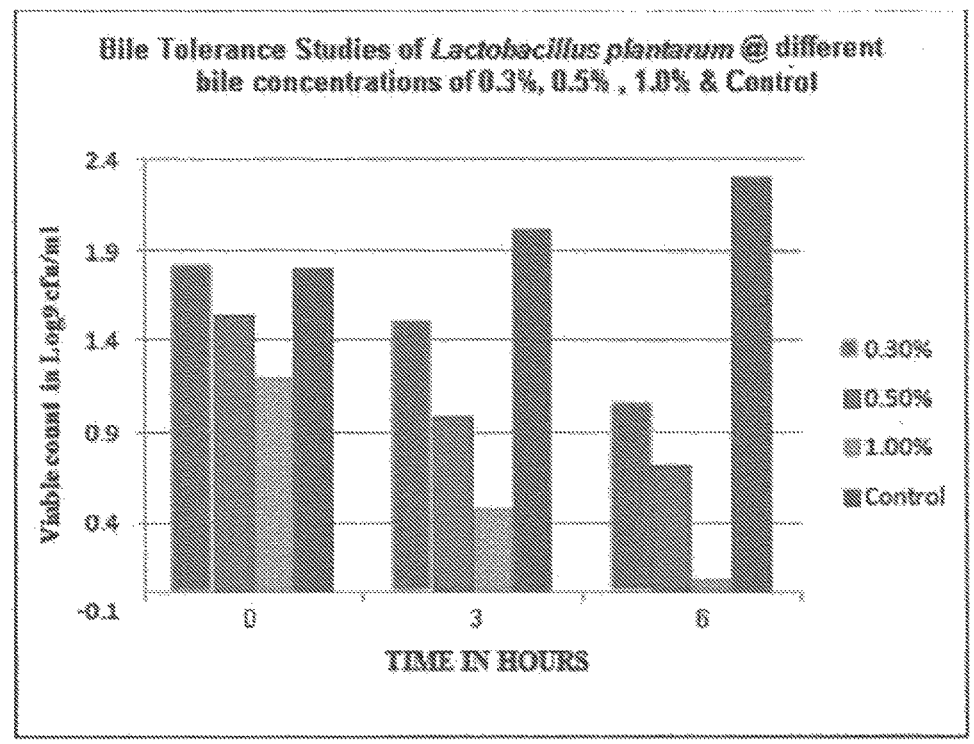
FIG. 11 depicts the Bile Tolerance of thermostable strain Lactobacillus plantarum TSP-Lp1 at different bile concentration values and time intervals.

From the above table and FIG. 11 of the present disclosure, it is clear that the LP strains of the present disclosure are capable of tolerating high concentrations of Bile. Thus, the thermo-stable strains of the present disclosure are suitable for being incorporated into food products and act beneficially in the environment of the stomach.

Example 13: Tests for the Identification of *Lactobacillus acidophilus*

In this study, identification studies are carried oust to ascertain the morphological, biochemical and physiological behavior of the strains of the present disclosure. As seen in the table below, the strain of *Lactobacillus acidophilus* TSP-La1 is identified as *Bacillus* (Rod), Gram-positive and non-motile.

Gram Staining Procedure

Materials Required

Clean glass slides, Inoculating loop, Bunsen burner, Microscope, Immersion oil, Saline and Cultures.

Reagents

1. Primary Stain—Crystal Violet
2. Mordant—Grams Iodine
3. Decolourizer—Ethyl Alcohol
4. Secondary Stain—Safranin Gram Stain Procedure 1. The slide with heat fixed smear is placed on staining tray.
2. The smear is flooded with crystal violet and kept aside for 1 minute.
3. The slide is tilted slightly and gently rinsed with tap water or distilled water using a wash bottle.
4. The smear is flooded with Gram's iodine and kept aside for 1 minute.
5. The slide is tilted slightly and gently rinsed with tap water or distilled water using a wash bottle. The smear appears as a purple circle on the slide.
6. It is decolorized using 95% ethyl alcohol or acetone. The slide is tilted slightly and the alcohol is applied drop by drop for 5 to 10 seconds until the alcohol runs almost clear.
7. The slide is immediately rinsed with water.
8. The slide is flooded with safranin to counter-stain and kept aside for 45 seconds.

TABLE 15

| | | Total plate counts ($\log_9$ CFU/mL) | | | | | |
|---|---|---|---|---|---|---|---|
| Strain | Bile Conc., | 0 hr | % of Viability | 3.0 hr | % of Viability | 6.0 hr | % of Viability |
| Lactobacillus | 0.3% | 1.80 | 100% | 1.50 | 83.33% | 1.06 | 58.33% |
| plantarum | 0.5% | 1.55 | 86.11% | 0.98 | 54.44% | 0.71 | 39.44% |
| TSP-La1(TPPL- | 1.0% | 1.20 | 66.66% | 0.48 | 26.66% | 0.09 | 5.0% |
| PLTHS100) | Control | 1.80 | 100% | 2.02 | 100% | 2.31 | 100% |

9. The slide is tilted slightly and gently rinsed with tap water or distilled water using a wash bottle.

10. The slide is blotted dry with bibulous paper.

11. The smear is viewed using a light-microscope under oil-immersion.

Motility Testing Procedure

Soft Agar Stabbing (Tube Method)

Materials Required

Two test tubes with Nutrient Agar medium

Inoculation Stab needle

Over night grown Cultures—18-24 hrs (*Lactobacillus acidophilus* & *Lactobacillus plantarum*)

Procedure

1. The tubes of Nutrient Agar media are labeled with the names of the organisms.
2. The inoculating stab needle is flamed and cooled and inserted into the culture after flaming the neck of the tube.
3. The cap is removed from the tube of medium, the neck is flamed, and stabbed ⅔ of the way down to the bottom. The neck of the tube is flamed again before returning the cap to the tube.
4. The tubes are incubated at 37° C. for 24 to 48 hours.
5. The cultures are examined for the presence or absence of a precipitate along the line of the stab inoculation.

TABLE 16

| PARAMETER | RESULTS |
|---|---|
| *Lactobacillus acidophilus* TSP-La 1 | |
| Morphology | *Bacillus* (Rod) |
| Gram Staining | + |
| Motility | Non Motile |
| Lactic Acid Production | + |
| Indole Test | − |
| Catalase Test | − |
| Gelatin Hydrolysis Test | − |
| Starch Hydrolysis Test | − |
| Sugar Fermentation Test | |
| Glucose (0.1%) | +/− |
| Dextrose (0.1%) | +/− |
| Sucrose (0.1%) | +/+ |
| FOS (0.1%) | +/− |
| Maltose (0.1%) | +/− |

"+" is Positive.
"−" is Negative.
"+/−" indicates the Production of Acid but does not produce Gas.
+/+" indicates the production of both Acid and Gas.

Example 14: Tests for the Identification of *Lactobacillus plantarum*

In this study, the same set of morphological, biological and physiological studies are conducted for the strain i.e. *Lactobacillus plantarum* TSP-Lp1 of the present disclosure. The table below lists the morphological and physiological characteristics of the LP strain.

TABLE 17

| PARAMETER | RESULTS |
|---|---|
| *Lactobacillus plantarum* TSP-Lp 1 | |
| Microscopy | *Bacillus* (Rod) |
| Gram Staining | + |
| Motility | Non Motile |
| Lactic Acid Production | + |

TABLE 17-continued

| PARAMETER | RESULTS |
|---|---|
| Indole Test | − |
| Catalase Test | − |
| Gelatin Hydrolysis Test | − |
| Starch Hydrolysis Test | − |
| SUGAR FERMENTATION TEST | |
| Glucose (0.1%) | +/− |
| Dextrose (0.1%) | +/− |
| Sucrose (0.1%) | +/− |
| FOS (0.1%) | +/− |
| Maltose (0.1%) | +/− |

"+" is Positive.
"−" is Negative.
"+/−" indicates the Production of Acid but does not produce Gas.
+/+" indicates the production of both Acid and Gas.

As seen in the table above, the strain of *Lactobacillus plantarum* TSP-Lp1 is identified as *Bacillus* (Rod), Gram-positive and non-motile.

Example 15: Carbohydrate Utilization

This example establishes that the thermo-stable strains of the present disclosure are able to utilize the nutrients and substrates in a normal diet.

Materials Required

1. Phenol Red Carbohydrate Fermentation Broth.
2. Bacterial culture.
3. Inoculation loop.
4. Incubator (37. C).

I. Preparation of Carbohydrate Fermentation Broth

1. The trypticase, Sodium chloride, and Phenol red is weighed and dissolved in 100 ml distilled water and transferred into conical flasks.
2. 0.5% to 1% of desired carbohydrate is added into all flasks.
3. Inverted Durham tubes are inserted into all tubes, and the Durham tubes should be fully filled with broth.
4. The tubes are sterilized at 121° C. for 20 minutes.
5. It is important to not overheat the Phenol red Carbohydrate fermentation broth. The overheating will result in breaking down of the molecules and form compounds with a characteristic color and flavor.
6. The sugar is transferred into screw capped tubes or fermentation tubes and labelled properly.

Ingredients of the Fermentation Broth:

1. Trypticase: 1 g
2. Carbohydrate: 0.5 g (Glucose, Dextrose, Sucrose, Maltose, Fructo Oligosaccharide (FOS)
3. Sodium Chloride: 0.5 g
4. Phenol red: 0.0189 mg Autoclaved at 121.0 for 20 minutes.

II. Inoculation of Bacterial Culture into the Phenol Red Carbohydrate Broth

1. Each labeled carbohydrate broth is aseptically inoculated with both the thermo-stable strains of the present disclosure and un-inoculated tubes as kept as control tubes.
2. The tubes are incubated at 18-24 hours at 37° C.
3. The reaction is observed and results are provided in FIG. 13 of the present disclosure.

Results of Carbohydrate Fermentation Test

Figure 13:
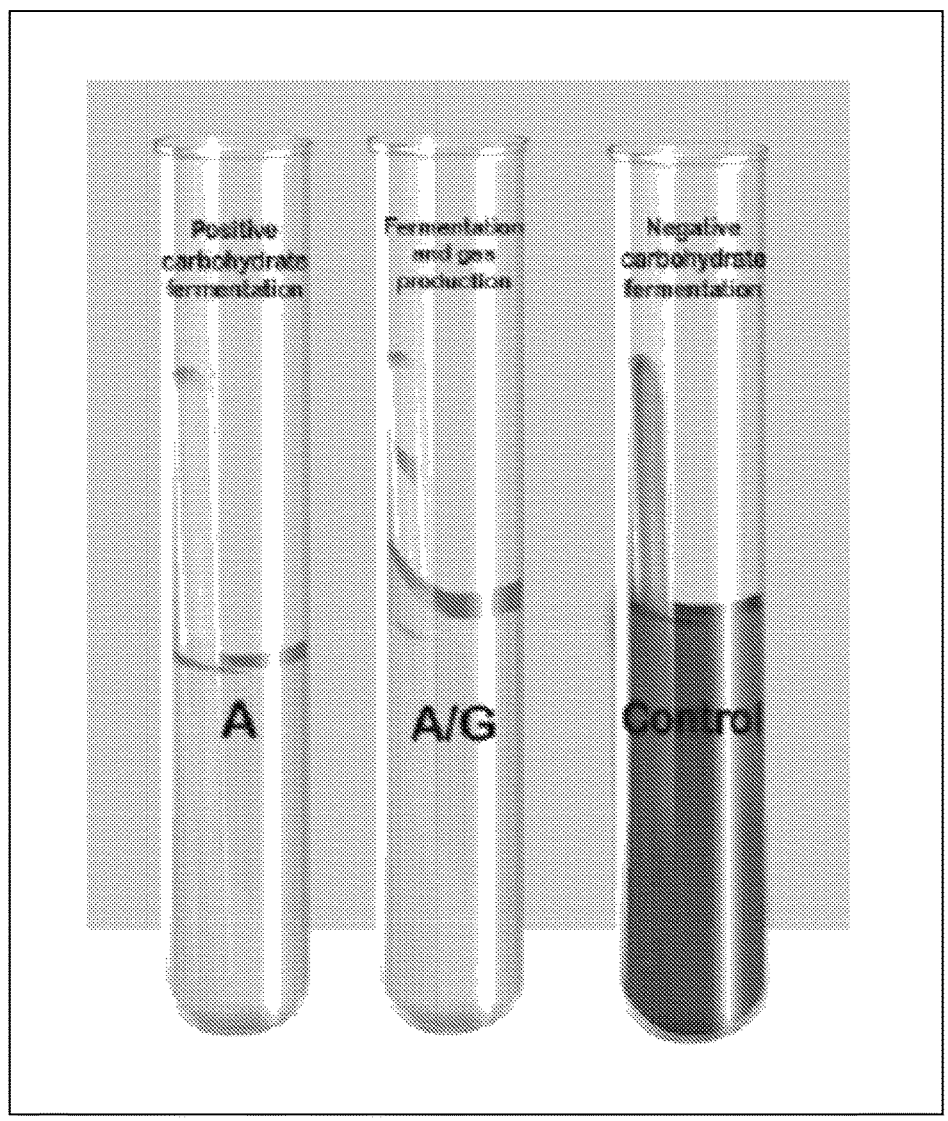
FIG. 13 depicts the results of carbohydrate fermentation test with thermostable strains of the present disclosure.

It is observed from FIG. 13 that after inoculation with either of the strains of the present disclosure, in the tubes:

1. Acid production: Changes the medium into yellow color—the organism ferments the given carbohydrate and produces organic acids thereby reducing the pH of the medium into acidic.

2. Acid and Gas production: Changes the medium into yellow color—the organism ferments the given carbohydrate and produce organic acids and gas. Gas production can be detected by the presence of small bubbles in the inverted Durham tubes.

3. Absence of fermentation in Control: The broth retains the red color. The organism is not present so carbohydrate is not utilized.

Thus, from this example, establishes that the thermostable strains of the present disclosure are able to utilize the nutrients and substrates in a normal diet and thus aids in providing general good health when consumed.

Example 16: Comparison with Commercially Available Strains

A) The objective of this experiment is to establish the stability of the temperature stable *Lactobacillus acidophilus* TSP-La1 strain of the present disclosure in comparison to commercially available Freeze dried *Lactobacillus acidophilus* at 70° C. in chocolates.

Temperature: 70° C.
Probiotic Strain: Temperature stable *Lactobacillus acidophilus* TSP-La1
Commercial strain: Freeze dried *Lactobacillus acidophilus*

TABLE 18

| Sl No. | PROBIOTIC STRAIN | LIMIT (MILLION CFU/ CHOCOLATE) | Viability (MILLION CFU/ CHOCOLATE) |
|---|---|---|---|
| 1. | *Lactobacillus acidophilus* TSP-La1 | Not less than 100 | 103 |
| 2. | Freeze dried *Lactobacillus acidophilus* | Not less than 100 | 00 |

B) The objective of this experiment is to establish the stability of the temperature stable *Lactobacillus plantarum* TSP-Lp1 strain of the present disclosure in comparison to commercially available Freeze dried *Lactobacillus plantarum* at 70° C. in chocolates.

Temperature: 70° C.
Probiotic Strain: Temperature stable *Lactobacillus plantarum* TSP-Lp1
Commercial strain: Freeze dried *Lactobacillus plantarum*.

TABLE 19

| Sl No. | PROBIOTIC STRAIN | LIMIT (MILLION CFU/ CHOCOLATE) | Viability (MILLION CFU/ CHOCOLATE) |
|---|---|---|---|
| 1. | *Lactobacillus plantarum* TSP-Lp1 | Not less than 100 | 105 |
| 2. | Freeze dried *Lactobacillus plantarum* | Not less than 100 | 00 |

It is observed from the table above that commercial strains as well as the strains of the present disclosure are present in chocolate at an amount more than 100 million cfu/chocolate. However, after heating the chocolate to 70° C., all the cells of the commercially available strain are destroyed, whereas the viability of the thermo-stable strains of the present disclosure is high. Thus, it is concluded that the strains of the present disclosure is viable and stable at 70° C. (Temperature used to make chocolates as prototype).

Example 17: Long Term Stability Studies

The objective of this example is to establish the stability of the thermo-stable strains of the present disclosure over a period of 1-9 months.

Example 17A

PRODUCT: *Lactobacillus acidophilus* TSP-La1
STABILITY STUDIES: At Room Temperature at 25±2° C.
PERIOD OF TESTING: 1, 2, 3, 6, 9, 12, 18, and 24 Months
QUANTITY: 50 gm

TABLE 20

| | Specification | Limits | Initial | 1st Month |
|---|---|---|---|---|
| 01. | Description | Beige to Light Brown Powder | Beige to Light Brown Powder | Beige to Light Brown Powder |
| 02. | Loss on Drying | NMT 5.0% | 3.2% | 3.6% |
| 03. | Total Yeast & Mold Count | NMT 100 cfu/gm | <10 cfu/gm | <10 cfu/gm |
| 04. | Total Viable Cell Count | NLT 1.5 B cfu/gm | 1.65 B cfu/gm | 1.60 B cfu/gm |
| 05. | Pathogens | Should be Absent/10 gm | Absent/10 gm | Absent/10 gm |

| | 2nd Month | 3rd Month | 6th Month | 9th Month |
|---|---|---|---|---|
| 01. | Beige to Light Brown Powder | Beige to Light Brown Powder | Beige to Light Brown Powder | Beige to Light Brown Powder |
| 02. | 3.8% | 4.1% | 4.5% | 4.79% |
| 03. | <10 cfu/gm | <10 cfu/gm | 10 cfu/gm | 10 cfu/gm |
| 04. | 1.60 B cfu/gm | 1.60 B cfu/gm | 1.55 B cfu/gm | 1.52 B cfu/gm |
| 05. | Absent/10 gm | Absent/10 gm | Absent/10 gm | Absent/10 gm |

NLT—Not less than
NMT—Not more than
B cfu/gm: Billion cfu/gm.

No significant changes are observed during the studies. Thus, it is concluded that the strain of the present disclosure *Lactobacillus acidophilus* TSP-La1 is stable for a period of up to 9 months at room temperature.

Example 17B

In this example, probiotic gummy with strain *Lactobacillus acidophilus* TSP-La1 is stored at 25±2.0 and relative humidity of 60±5% relative humidity. Tests are performed for color and flavor. Assays are also performed. The tests are performed each month for a period of 6 months.
Assay A—Total yeast and mould count.
Assay B—Total viable cell count.
The results are provided below.

TABLE 21

| Period of Testing | Colour | Flavour | Assay A | Assay B |
|---|---|---|---|---|
| Initial | Red | Mixed Berry | <10 | 490 |
| 1st Month | Red | Mixed Berry | <10 | 507 |
| 2nd Month | Red | Mixed Berry | <10 | 500 |
| 3rd Month | Red | Mixed Berry | <10 | 490 |
| 4th Month | Red | Mixed Berry | <15 | 480 |
| 5th Month | Red | Mixed Berry | 20 | 480 |
| 6th Month | Red | Mixed Berry | 20 | 470 |
| LIMITS | Red | Mixed Berry | NMT 100 cfu/g | NLT 450 Million cfu/gummy |

NLT—Not less than
RT—Room Temperature
NMT—Not more than

No Significant change is observed during the studies. Thus, the probiotic strain containing product is stable at Room temperature condition for 6 months.

Example 18: Stability Studies in Cookies

The objective of this example is to establish the stability of the thermo-stable strains of the present disclosure in cookies at 20° C. for a period of 6 days.

Probiotic cookies are prepared with a blend of 2 strains *Lactobacillus acidophilus* TSP-La1 & *Lactobacillus plantarum* TSP-Lp1 of the present disclosure at 12.5 gm each Cookie. The stability studies are carried out at 20±2° C. and the humidity is maintained at 50±5%. The results are provided in the table below.

TABLE 22

| SI No | Test Parameters | Limits | Initial | Day 1 | Day 2 | Day 4 | Day 5 | Day 6 |
|---|---|---|---|---|---|---|---|---|
| 01. | Total Viable Cell Count | NLT 5.0 Billion cells/cookie | 4.0 Billion cells/cookie | 4.10 Billion cells/cookie | 4.46 Billion cells/cookie | 4.50 Billion cells/cookie | 4.63 Billion cells/cookie | 4.86 Billion cells/cookie |

It is concluded from the table above that the strains of the present disclosure are viable for up to 97.2% for 6 days at 20° C.

Example 19: Genome Sequence of the Thermostable Strains

In this example, the 16S rRNA gene sequencing of the strains of the present disclosure is provided. The thermostable microorganism *Lactobacillus plantarum* has genomic sequence set forth in SEQ ID No.1. The thermostable microorganism *Lactobacillus acidophilus* has genomic sequence set forth in SEQ ID No.2.

```
SEQ ID No. 1-Lactobacillus plantarum TSP-Lp1
AATCATCTGT CCACCTTAAG GCGGCTGGGT TCCTAAAAGGG
TTACCCCACC GACTTTGGGT GGTTACAAAC TCTCATGGGT
GTGACGGGCG GTGTGTACAA GGCCCGGGAA CGTATTCACC
GCGGCATGCT GATCCGCGAT TACTAGCGAT TCCGACTTCA
TGTAGGCGAG TTGCAGCCTA CAATCCGAAC TGAGAATGGC
TTTAAGAGAT TAGCTTACTC TCGCGAGTTC GCAACTCGTT
GTACCATCCA TTGTAGCACG TGTGTAGCCC AGGTCATAAG
GGGCATGATG ATTTGACGTC ATCCCCACCT TCCTCCGGTT
TGTCACCGGC AGTCTCACCA GAGTGCCCAA CTTAATGCTG
GCAACTGATA ATAAGGGTTG CGCTCGTTGC GGGACTTAAC
CCAACATCTC ACGACACGAG CTGACGACAA CCATGCACCA
CCTGTATCCA TGTCCCCGAA GGGAACGTCT AATCTCTTAG
ATTTGCATAG TATGTCAAGA CCTGGTAAGG TTCTTCGCGT
AGCTTCGAAT TAAACCACAT GCTCCACCGC TTGTGCGGGCC
CCCGTCAATTC CTTTGAGTTT CAGCCTTGCG GCCGTACTCC
CCAGGCGGAA TGCTTAATGC GTTAGCTGCA GCACTGAAGG
GCGGAAACCC TCCAACACTT AGCATTCATC GTTTACGGTA
TGGACTACCA GGGTATCTAA TCCTGTTTGC TACCCATACT
TTCGAGCCTC AGCGTCAGTT ACAGACCAGA CAGCCGCCTT
CGCCACTGGT GTTCTTCCAT ATATCTACGC ATTTCACCGC
TACACATGGA GTTCCACTGT CCTCTTCTGC ACTCAAGTTT
CCCAGTTTCC GATGCACTTC TTCGGTTGAG CCGAAGGCTT
TCACATCAGA CTTAAAAAAC CGCCTGCGCT CGCTTTACGC
CCAATAAATC CGGACAACGC TTGCCACCTA CGTATTACCG
CGGCTGCTGG CACGTAGTTA GCCGTGGCTT TCTGGTTAAA
TACCGTCAAT ACCTGAACAG TTACTCTCAG ATATGTTCTT
CTTTAACAAC AGAGTTTTAC GAGCCGAAAC CCTTCTTCAC
-continued
TCACGCGGCG TTGCTCCATC AGACTTTCGT CCATTGTGGA
AGATTCCCTA CTGCTGCCTC CCGTAGGAGT TTGGGCCGTG
TCTCAGTCCC AATGTGGCCG ATTACCCTCT CAGGTCGGCT
ACGTATCATT GCCATGGTGA GCCGTTACCC CACCATCTAG
CTAATACGCC GCGGGACCAT CCAAAAGTGA TAGCCGAAGC
CATCTTTCAA ACTCGGACCA TGCGGTCCAA GTTGTTATGC
```

```
GGTATTAGCA TCTGTTTCCA GGTGTTATCC CCCGCTTCTG

GGCAGGTTTC CCACGTGTTA CTCACCAGTT CGCCACTCAC

TCAAATGTA AATCATGATG CAAGCACCAA TCAATACCAG

AGTTCGTTCG ACTTGCATGT ATTAGGCACG CCGCCAGCGT

TCGTCCT

SEQ ID No. 2-Lactobacillus acidophilus TSP-La1
AGAGTTTGCA ATGCCCAAAG CCGGTGGCCT AACCTTCGGC

AAGGAGCCGA CT AAGGCAGG GCAGATGACT GGGGTGAAGT

CCTAACAAGG TAGCCGTACG AGAACCTGCG GCTGGATCAC

CTCCTTTCTA AGGAAGCGAA GGATATGGAG AGTAGAAATA

CTAAGAGAAG TATCCAGAGC AAGCGGAAGC ACACTGAGAA

ACTTTGCTTA GTTTTGAGGG TAACTCCTCA AGAGAGTTAC

TACATTGAAA ACTGAATATA ATCCAATCAA AACACCGCCA

CACTAAAGGA GAACATACTG TAGAGCGACC GATAACGAA

TTCTTAATT AGGTCAAGTA GAAAAGGGCG CACGGTGAAT

GCCTTGGCAC TGAAAGCCGA TGAAGGACGC GACTAACTAC

GAAAGTCTTC GGGAGCCGT AAGTAGGCTT TGATCCGGAG

GTCTCCGAAT GGGGAACCCA GCATGTGCAG AATGCTATCC

TTAAGTGAAT ACATAGCTTA AGGAGGGAAC ACGCAGCGA
```

In view of the above examples and results, it is evident that the strain(s) of the present disclosure when incorporated in the food products are viable at high temperatures.

Thus, the thermo-stable strain(s) of the present disclosure eliminate the requirement of cold storage and thus are economical and at the same time provide for enhanced nutrition to the consumers.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

---

We claim:

1. A food product comprising a thermostable *Lactobacillus* microorganism, wherein the thermostable microorganism is selected from the group consisting of *Lactobacillus plantarum* with ATCC SD No. 6863 comprising genomic sequence set forth in SEQ ID No.1 and *Lactobacillus acidophilus* with ATCC SD No. 6864 comprising genomic sequence set forth in SEQ ID No.2.

2. A method of preparing a food product, said method comprising combining a thermostable strain selected from the group consisting of *Lactobacillus plantarum* with ATCC SD No. 6863 comprising genomic sequence set forth in SEQ ID No.1 and *Lactobacillus acidophilus* with ATCC SD No. 6864 comprising genomic sequence set forth in SEQ ID No.2; with a component of the food product during or after preparation of the food product.

3. The food product as claimed in claim 1, wherein the food product is selected from the group consisting of beverage, yogurt, dairy product, nectar, fruit juice, energy drink, bakery food, chocolate, cereal and soup.

4. The food product as claimed in claim 1, wherein the thermostable microorganism is viable at temperature ranging from about 25° C. to 250° C.

5. A thermostable *Lactobacillus* microorganism selected from the group consisting of *Lactobacillus plantarum* with ATCC SD No. 6863 comprising genomic sequence set forth in SEQ ID No.1 and *Lactobacillus acidophilus* with ATCC SD No. 6864 comprising genomic sequence set forth in SEQ ID No.2.

6. The thermostable microorganism as claimed in claim 5, wherein the thermostable microorganism includes the *Lactobacillus plantarum* with ATCC SD No. 6863.

7. The thermostable microorganism as claimed in claim 5, wherein the thermostable microorganism includes the *Lactobacillus acidophilus* with ATCC SD No. 6864.

8. The thermostable microorganism as claimed in claim 5, wherein the thermostable microorganism is viable at temperature ranging from about 25° C. to 250° C.

9. The method as claimed in claim 2, wherein the food product is selected from the group consisting of beverage, yogurt, dairy product, nectar, fruit juice, energy drink, bakery food, chocolate, cereal and soup.

10. The method as claimed in claim 2, wherein the thermostable microorganism is viable at temperature ranging from about 25° C. to 250° C.

11. The method as claimed in claim 2, wherein the thermostable microorganism includes the *Lactobacillus plantarum* with ATCC SD No. 6863.

12. The method as claimed in claim 2, wherein the thermostable microorganism includes the *Lactobacillus acidophilus* with ATCC SD No. 6864.

* * * * *

SEQUENCE LISTING

```
<160> NUMBER OF SEQ ID NOS: 2

<210> SEQ ID NO 1
<211> LENGTH: 1489
<212> TYPE: DNA
<213> ORGANISM: Lactobacillus plantarum
<220> FEATURE:
<221> NAME/KEY: gene
<222> LOCATION: (1)..(1489)

<400> SEQUENCE: 1
aatcatctgt ccaccttaag gcggctgggt tcctaaaagg gttacccac cgactttggg      60 tggttacaaa ctctcatggg tgtgacgggc ggtgtgtaca aggcccggga acgtattcac     120
cgcggcatgc tgatccgcga ttactagcga ttccgacttc atgtaggcga gttgcagcct    180
acaatccgaa ctgagaatgg ctttaagaga ttagcttact ctcgcgagtt cgcaactcgt    240
tgtaccatcc attgtagcac gtgtgtagcc caggtcataa ggggcatgat gatttgacgt    300 catcccacc ttcctccggt ttgtcaccgg cagtctcacc agagtgccca acttaatgct     360
ggcaactgat aataagggtt gcgctcgttg cgggacttaa cccaacatct cacgacacga    420
gctgacgaca accatgcacc acctgtatcc atgtccccga agggaacgtc taatctctta    480
gatttgcata gtatgtcaag acctggtaag gttcttcgcg tagcttcgaa ttaaaccaca    540
tgctccaccg cttgtgcggg ccccgtcaa ttcctttgag tttcagcctt gcggccgtac     600
tccccaggcg gaatgcttaa tgcgttagct gcagcactga agggcggaaa ccctccaaca    660
cttagcattc atcgtttacg gtatggacta ccagggtatc taatcctgtt tgctacccat    720
```

```
actttcgagc ctcagcgtca gttacagacc agacagccgc cttcgccact ggtgttcttc    780
catatatcta cgcatttcac cgctacacat ggagttccac tgtcctcttc tgcactcaag    840
tttcccagtt tccgatgcac ttcttcggtt gagccgaagg ctttcacatc agacttaaaa    900
aaccgcctgc gctcgcttta cgcccaataa atccggacaa cgcttgccac ctacgtatta    960
ccgcggctgc tggcacgtag ttagccgtgg ctttctggtt aaataccgtc aatacctgaa   1020
cagttactct cagatatgtt cttctttaac aacagagttt tacgagccga aaccccttctt   1080 cactcacgcg gcgttgctcc atcagacttt cgtccattgt ggaagattcc ctactgctgc   1140
ctcccgtagg agtttgggcc gtgtctcagt cccaatgtgg ccgattaccc tctcaggtcg   1200
gctacgtatc attgccatgg tgagccgtta ccccaccatc tagctaatac gccgcgggac   1260
catccaaaag tgatagccga agccatcttt caaactcgga ccatgcggtc caagttgtta   1320
tgcggtatta gcatctgttt ccaggtgtta tcccccgctt ctgggcaggt ttcccacgtg   1380
ttactcacca gttcgccact cactcaaatg taaatcatga tgcaagcacc aatcaatacc   1440
agagttcgtt cgacttgcat gtattaggca cgccgccagc gttcgtcct              1489

<210> SEQ ID NO 2
<211> LENGTH: 516
<212> TYPE: DNA
<213> ORGANISM: Lactobacillus acidophilus
<220> FEATURE:
<221> NAME/KEY: gene
<222> LOCATION: (1)..(516)

<400> SEQUENCE: 2
agagtttgca atgcccaaag ccggtggcct aaccttcggc aaggagccga ctaaggcagg     60
gcagatgact ggggtgaagt cctaacaagg tagccgtacg agaacctgcg gctggatcac    120
ctcctttcta aggaagcgaa ggatatggag agtagaaata ctaagagaag tatccagagc    180
aagcggaagc acactgagaa actttgctta gttttgaggg taactcctca agagagttac    240
tacattgaaa actgaatata atccaatcaa aacaccgcca cactaaagga gaacatactg    300
tagagcgacc gataacgaat tcttaattag gtcaagtaga aaaggcgca cggtgaatgc     360 cttggcactg aaagccgatg aaggacgcga ctaactacga aagtcttcgg gagccgtaag    420
taggctttga tccggaggtc tccgaatggg gaacccagca tgtgcagaat gctatcctta    480
agtgaataca tagcttaagg agggaacacg cagcga                             516
```